(12) United States Patent
Bjerken

(10) Patent No.: US 7,708,747 B2
(45) Date of Patent: May 4, 2010

(54) ENDOSCOPIC SUTURING AND IMPLANT SYSTEM

(75) Inventor: David Bjerken, Marietta, GA (US)

(73) Assignee: InTailor Surgical, Inc., Marietta, GA (US)

( * ) Notice: Subject to any disclaimer, the term of this patent is extended or adjusted under 35 U.S.C. 154(b) by 427 days.

(21) Appl. No.: 11/783,875

(22) Filed: Apr. 12, 2007

(65) Prior Publication Data
US 2007/0244493 A1 Oct. 18, 2007

Related U.S. Application Data

(60) Provisional application No. 60/791,214, filed on Apr. 12, 2006.

(51) Int. Cl.
*A61B 17/04* (2006.01)
*A61B 17/10* (2006.01)

(52) U.S. Cl. .................................. 606/144; 606/139
(58) Field of Classification Search .............. 606/144, 606/139; 600/104, 139, 146, 149
See application file for complete search history.

(56) References Cited

U.S. PATENT DOCUMENTS

| 5,938,588 | A * | 8/1999 | Grabover et al. ............ 600/150 |
| 6,464,707 | B1 * | 10/2002 | Bjerken ....................... 606/139 |
| 2002/0107530 | A1 * | 8/2002 | Sauer et al. .................. 606/139 |
| 2006/0253126 | A1 * | 11/2006 | Bjerken et al. ............... 606/139 |

* cited by examiner

*Primary Examiner*—(Jackie) Tan-Uyen T Ho
*Assistant Examiner*—Christina Lauer

(57) ABSTRACT

Disclosed is a method and device for suturing tissue and implanting prosthetic grafts, the device includes 1) at least one flexible cannula having a means to remotely manipulate the configuration of its distal end, and 2) a suction capsule component that may be incorporated or fit within or about the flexible cannula. The flexible cannula and suction capsule component are of a size that allows them to be inserted, independently or as a unit, into a natural body orifice or small surgical incision. The suction component may be used to draw tissue into an opening in the suction capsule component, enabling the at least one needle to be advanced through the at least one flexible cannula thereby passing through the tissue held by the at least one opening in the suction capsule component and thereby delivering the attached suture to the tissue.

11 Claims, 31 Drawing Sheets

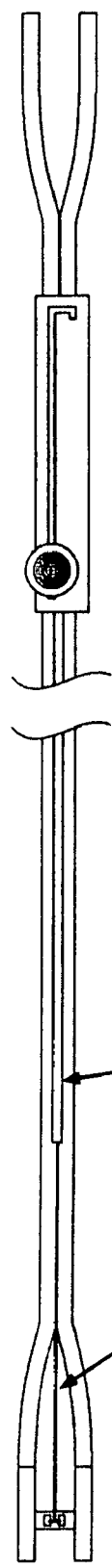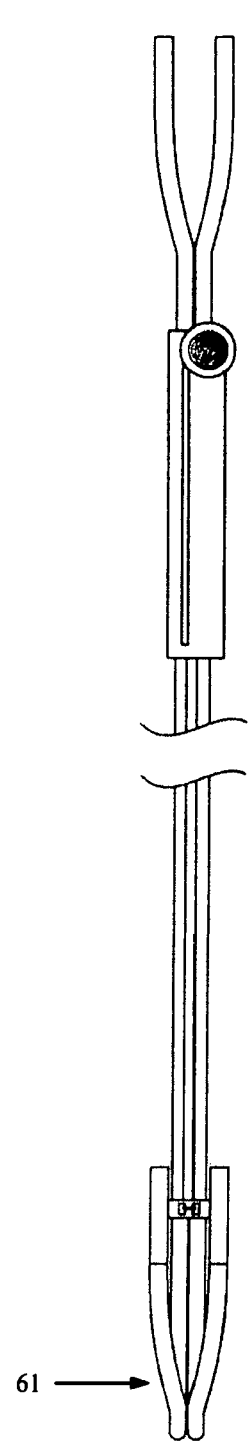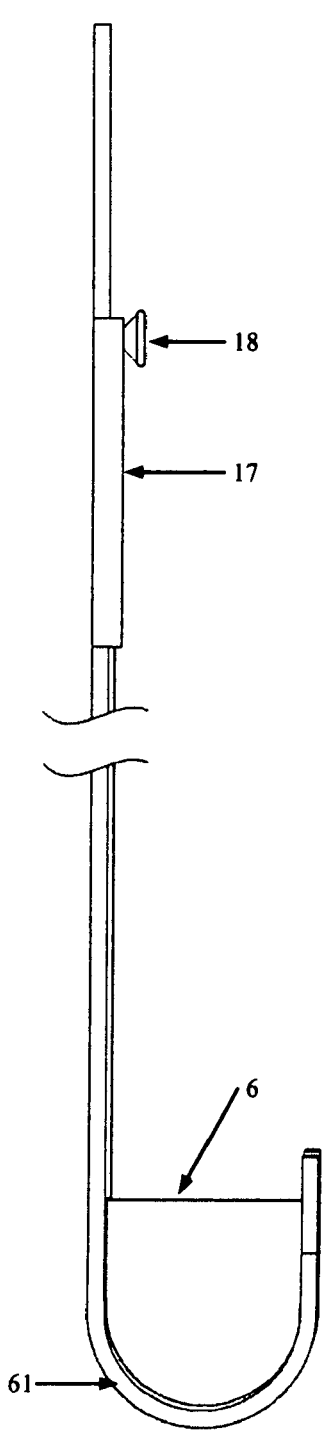
FIG. 4A  FIG. 4B  FIG. 4C  FIG. 4D

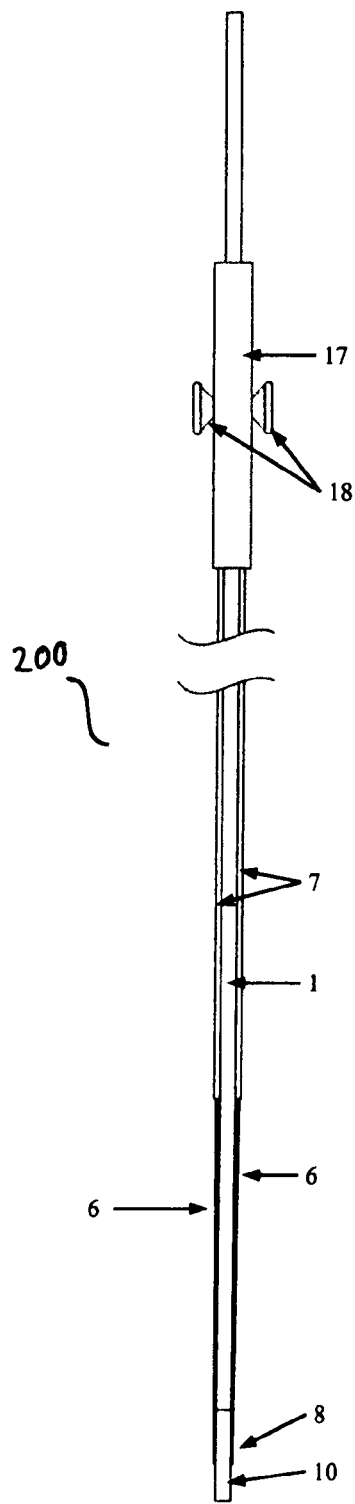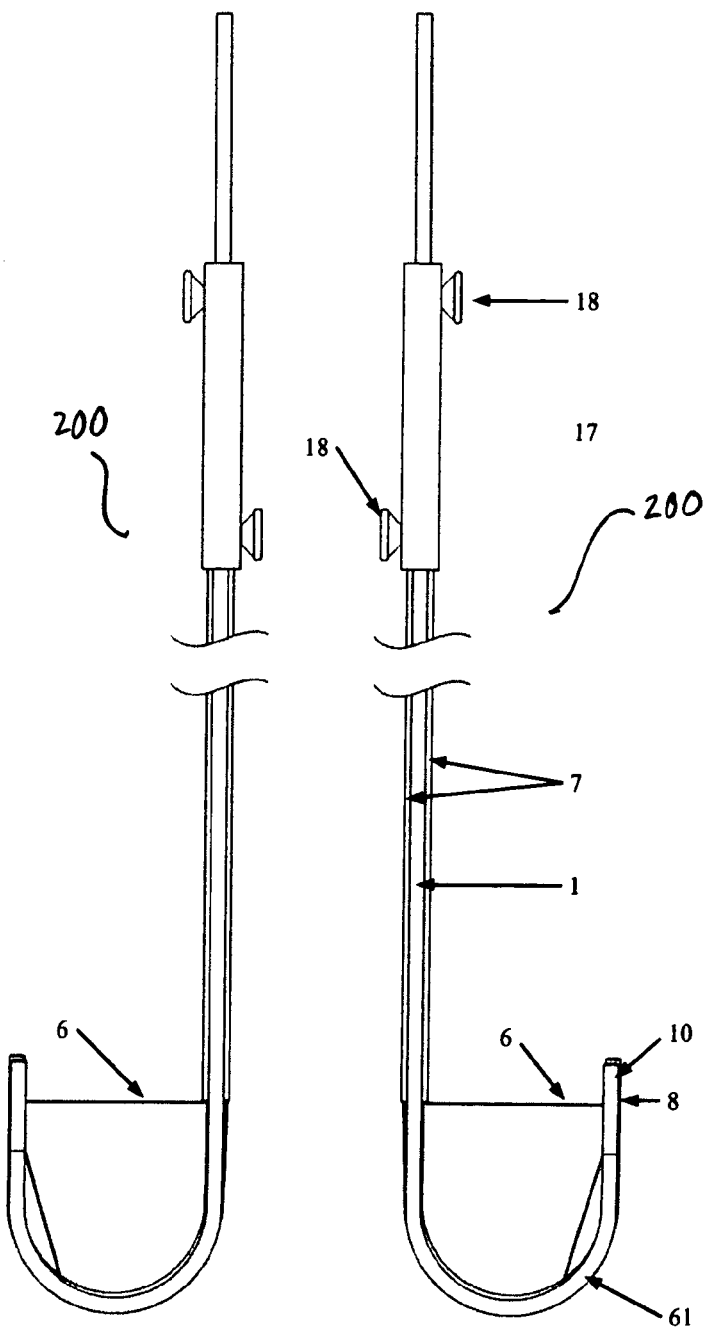
FIG. 5A  FIG. 5B  FIG. 5C

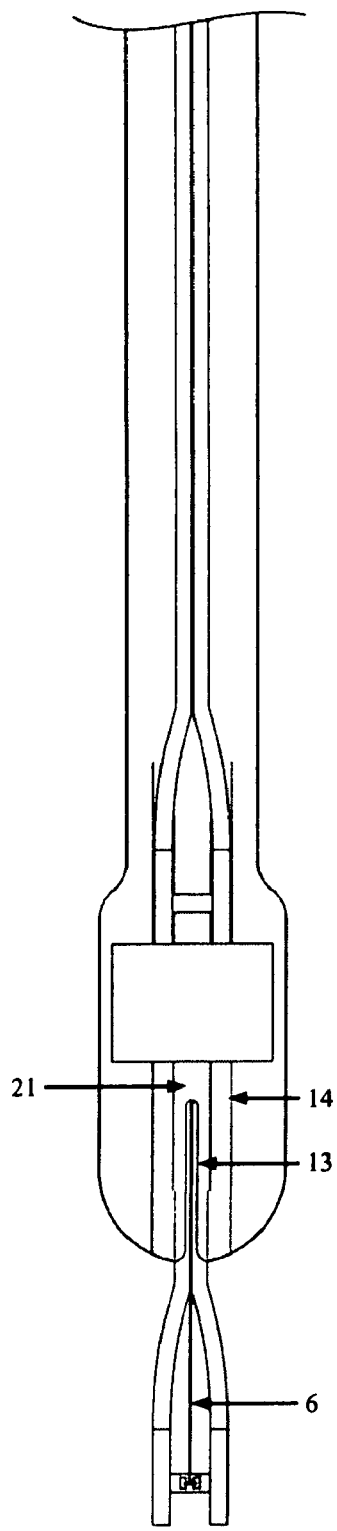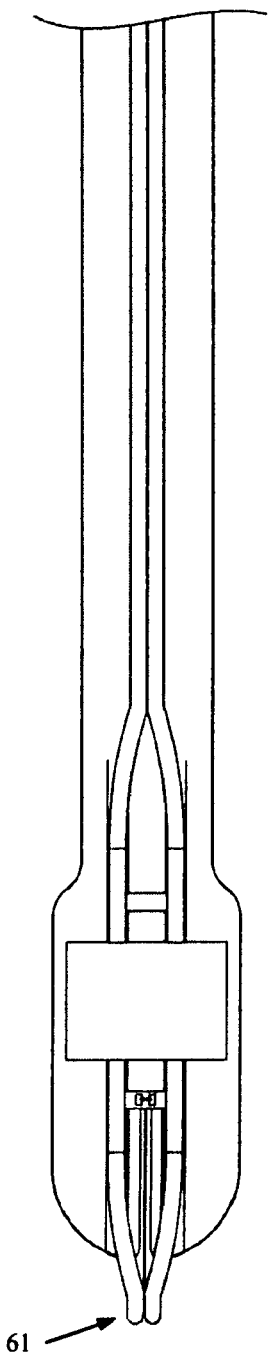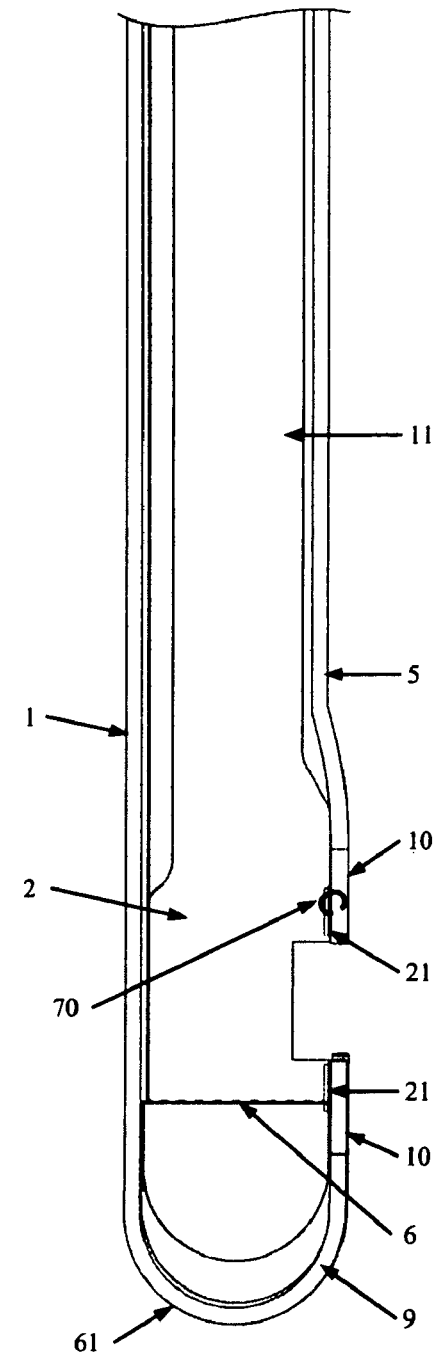
FIG. 7A  FIG. 7B  FIG. 7C

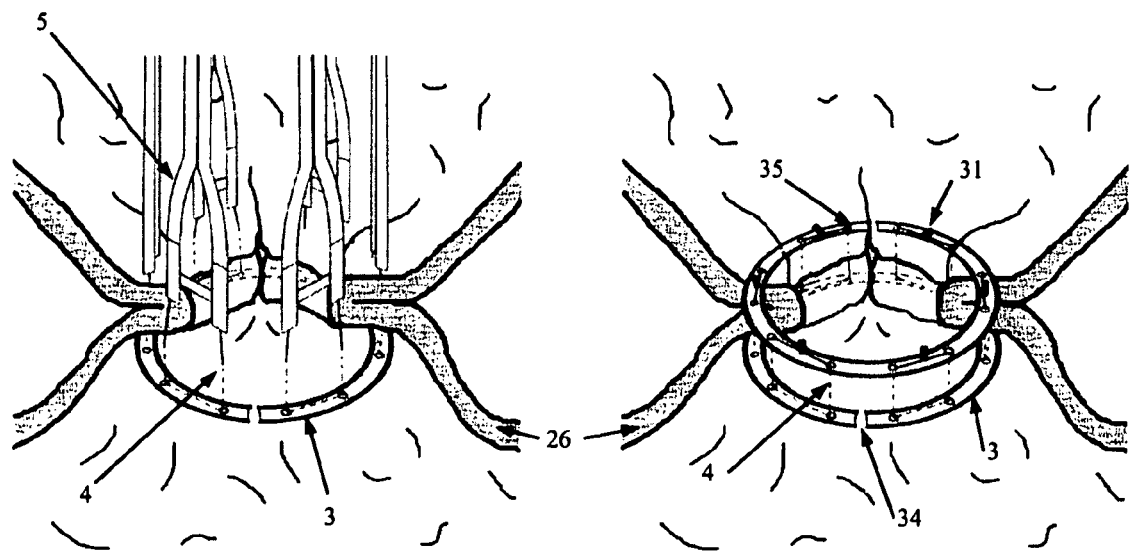
FIG. 17A  FIG. 17B
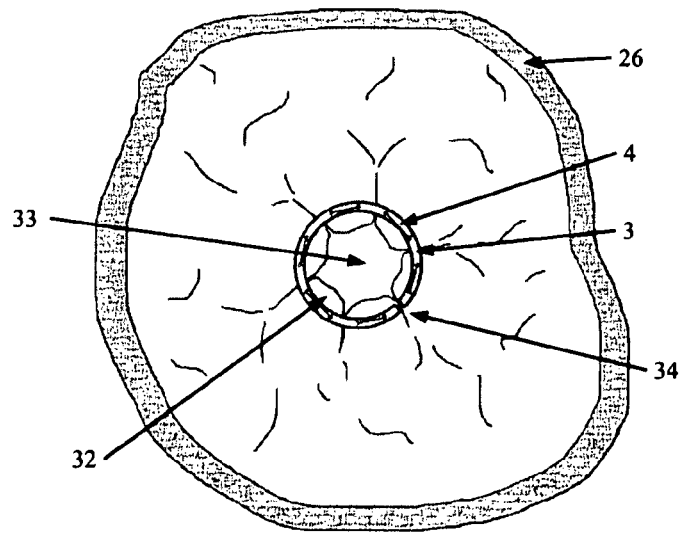
FIG. 17C

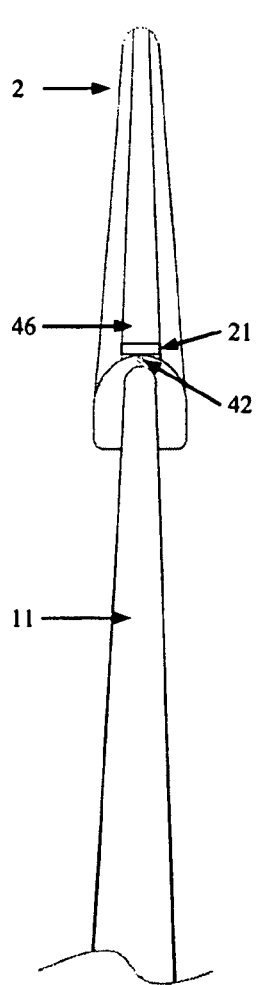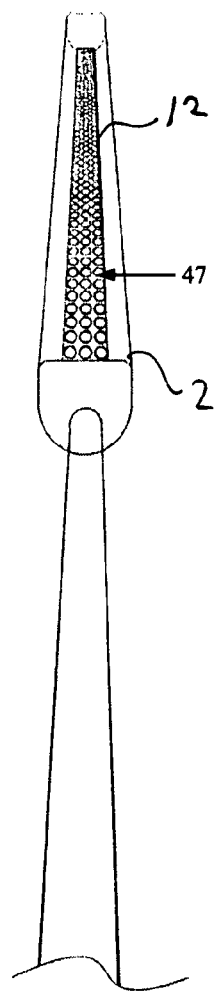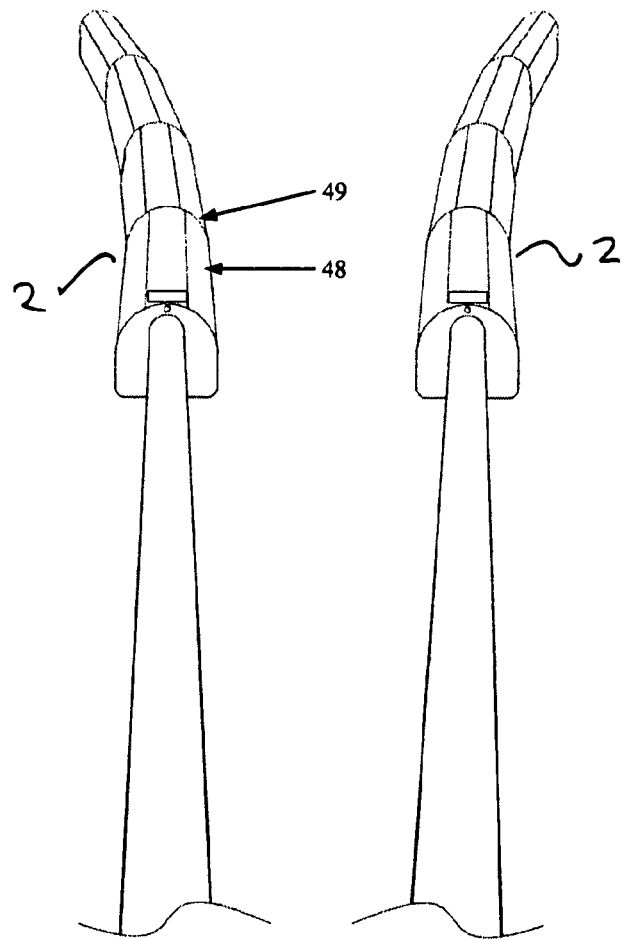
FIG. 23A   FIG. 23B   FIG. 23C   FIG. 23D

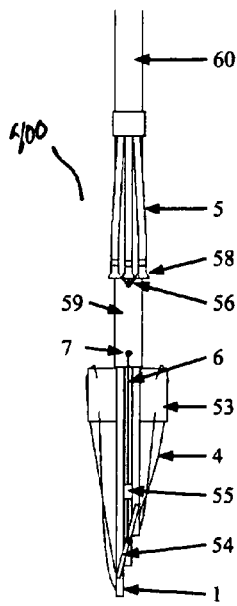
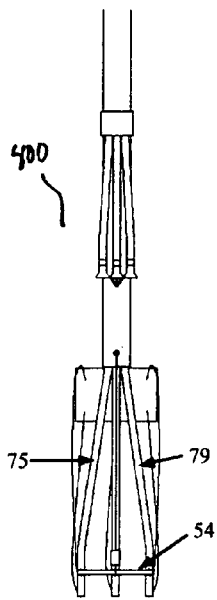
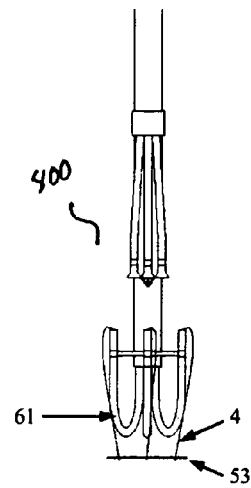
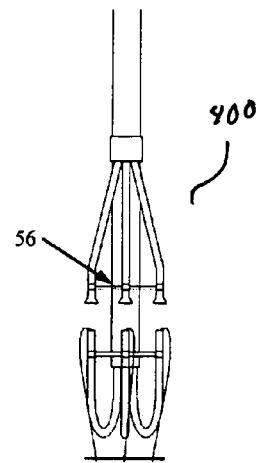
FIG. 29A  FIG. 29B  FIG. 29C  FIG. 29D
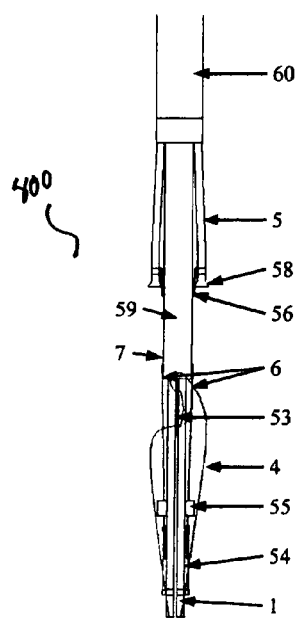
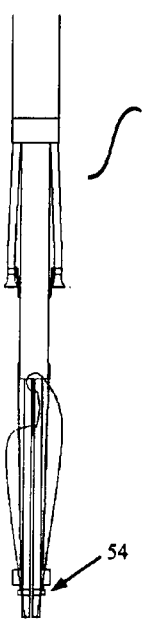
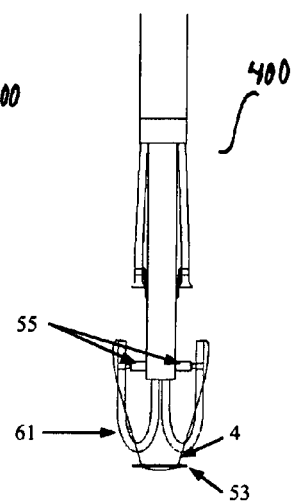
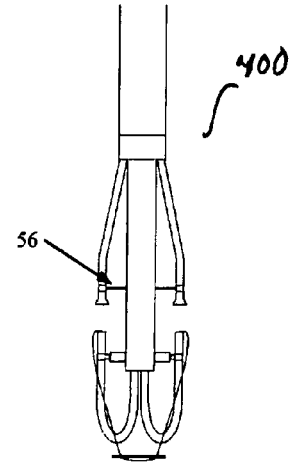
FIG. 30A  FIG. 30B  FIG. 30C  FIG. 30D

ENDOSCOPIC SUTURING AND IMPLANT SYSTEM

CROSS-REFERENCE TO RELATED APPLICATIONS

This application claims the benefit of U.S. Provisional Patent Application No. 60/791,214, filed on Apr. 12, 2006, which is hereby incorporated by reference for all purposes as if fully set forth herein.

BACKGROUND OF THE INVENTION

1. Field of the Invention

This invention relates in general to endoluminal surgical procedures for the treatment and control of obesity and, more particularly, to devices and method for the endoscopic implantation of suture and incorporated prosthetic grafts.

2. Discussion of the Related Art

Methods that have been used to treat obesity, which include gastric bypass and small bowel bypass surgery. Stapling of portions of the stomach has also been used to treat morbid obesity, which includes both vertical and horizontal stapling and other variations that are intended to reduce the size of the stomach and make a small stoma opening. Many problems have been associated with the use of staples. First, staples are undependable. Second, they may cause perforations in the stomach wall. And third, the pouch or the stoma formed by the staples may become enlarged over time, making the procedure useless.

Another related art method for weight control employs the placement of a band around a portion of the stomach by open or laparoscopic surgery thereby compressing the stomach and creating a stoma that is less than the normal interior diameter of the stomach. The constricted stoma restricts food intake into the lower digestive portion of the stomach. Such a band has been described by Kuzmak et al in U.S. Pat. Nos. 4,592,339, 5,074,868, and 5,226,429.

These devices, known as gastric bands, require a surgical procedure for their implantation, which includes accessing the patient's stomach and other internal organs via incisions. The morbidity related to these surgical procedures can cause pain, prolonged recovery, complications, and expense to the patient and to the healthcare system. The procedure can also be technically challenging for the surgeon.

Suturing devices described by Bjerken in U.S. Pat. No. 6,464,707 and in U.S. patent application Ser. Nos. 11/267,266 & 11/267,321 & 11/327,348 enable an operator to remotely place suture material within a closed space such a hollow body organ. Such devices enable the endoluminal implantation of prostheses, correction of defects, and the reconfiguration of tissue without the need for surgical incisions. U.S. Pat. No. 6,464,707 and U.S. patent application Ser. Nos. 11/267,266 & 11/267,321 & 11/327,348 are hereby incorporated by reference in their entirety as if fully set forth herein.

SUMMARY OF THE INVENTION

The present invention provides an endoscopic suturing and implant system that obviates one or more of the aforementioned problems due to the limitations of the related art.

Accordingly, one advantage of the present invention is that it reduces the invasiveness of suturing within hollow organ or body cavity.

Another advantage of the present invention is that it reduces the complications from abdominal surgical procedures such as gastric bypass surgery.

Another advantage of the present invention is that it minimizes or eliminates the incisions required to perform gastric bypass surgery.

Additional advantages of the invention will be set forth in the description that follows, and in part will be apparent from the description, or may be learned by practice of the invention. The advantages of the invention will be realized and attained by the structure pointed out in the written description and claims hereof as well as the appended drawings.

To achieve these and other advantages, the present invention involves a device for suturing within a hollow organ. The device comprises a delivery cannula; a receiving cannula; and a suction component having a suction port, wherein the delivery cannula has a delivery cannula distal end that is configured to be disposed on one side of the suction port, and wherein the receiving cannula has a receiving cannula distal end that is configured to be disposed on a second side of the suction port, and wherein suction component is releasably held to the delivery cannula and the receiving cannula.

In another aspect of the present invention, the aforementioned and other advantages are achieved by a method of suturing within a hollow organ. The method comprises inserting a flexible cannula into the hollow organ; inserting a tissue grabbing and holding device into the hollow organ; attaching the tissue grabbing and holding device to the flexible cannula at a distal end of the flexible cannula; applying a vacuum to the suction capsule; and advancing a flexible needle through the flexible cannula, wherein the flexible needle is coupled to a suture.

In another aspect of the present invention, the aforementioned and other advantages are achieved by a device for suturing within a hollow organ. The device comprises a plurality of cannula units, wherein each cannula unit has a delivery cannula, a receiving cannula, and a frame; and a suction component having a suction port, wherein the frame of each of the plurality of cannula unit is coupled to the suction component, and wherein a delivery cannula distal end and a receiving cannula distal end of each cannula unit are each disposed on an opposite side of the suction port such that a line between the delivery cannula distal end and the receiving cannula distal end is substantially perpendicular to a long dimension of the suction component.

BRIEF DESCRIPTION OF DRAWINGS

The accompanying drawings, which are included to provide a further understanding of the invention and are incorporated in and constitute a part of this specification, illustrate embodiments of the invention and together with the description serve to explain the principles of the invention.

FIG. 4A illustrates a front view of a delivery cannula set.

FIG. 4B illustrates a side view of a delivery cannula set.

FIG. 4C illustrates a front view of a delivery cannula set with the distal end warped.

FIG. 4D illustrates a side view of a delivery cannula set with the distal end warped.

FIG. 5A illustrates a side view of a multi-directional warping delivery cannula set.

FIG. 5B illustrates a side view of a multi-directional warping delivery cannula set with distal end warped in one direction.

FIG. 5C illustrates a side view of a multi-directional warping delivery cannula set with distal end warped in the opposite direction of FIG. 5B.

FIG. 7A illustrates a front view of a suction capsule component positioned in front of a delivery cannula set in a straight configuration.

FIG. 7B illustrates a font view of a suction capsule component incorporated with a warped delivery cannula set.

FIG. 7C illustrates a side view of a suction capsule component incorporated with a warped delivery cannula set.

FIG. 17A illustrates a sectional view of a distal graft incorporated into folds of tissue with the sutures maintained by a series of receiving cannula sets.

FIG. 17B illustrates a sectional view of distal and proximal grafts incorporated and secured into tissue folds.

FIG. 17C illustrates a cross-sectional view of the distal stomach pouch and the position of the distal graft.

FIG. 23A illustrates a top view of a linear suction capsule component.

FIG. 23B illustrates a bottom view of a linear suction capsule component.

FIG. 23C illustrates a view of an articulating linear suction capsule component configured in one direction.

FIG. 23D illustrates a view of an articulating linear suction capsule component configured in a direction opposite of FIG. 23C.

FIG. 29A illustrates a front view of an embodiment of the invention that delivers sutures within a hollow organ to close an incision or defect.

FIG. 29B illustrates a front view of an embodiment of the invention that delivers sutures within a hollow organ to close an incision or defect with the delivery cannula tips spread.

FIG. 29C illustrates a front view of an embodiment of the invention that delivers sutures within a hollow organ to close an incision or defect with the delivery cannula tips spread and warped upwards.

FIG. 29D illustrates a front view of an embodiment of the invention that delivers sutures within a hollow organ to close an incision or defect with the delivery cannula tips spread and warped upwards and the receiving cannula tips extended.

FIG. 30A illustrates a side view of an embodiment of the invention that delivers sutures within a hollow organ to close an incision or defect.

FIG. 30B illustrates a side view of an embodiment of the invention that delivers sutures within a hollow organ to close an incision or defect with the delivery cannula tips spread.

FIG. 30C illustrates a side view of an embodiment of the invention that delivers sutures within a hollow organ to close an incision or defect with the delivery cannula tips spread and warped upwards.

FIG. 30D illustrates a side view of an embodiment of the invention that delivers sutures within a hollow organ to close an incision or defect with the delivery cannula tips spread and warped upwards and the receiving cannula tips extended.

DETAILED DESCRIPTION OF INVENTION

The present invention provides a method and device for suturing tissue and implanting grafts within a hollow organ or closed body cavity such as the stomach. As used herein, "hollow organ" may refer to any hollow organ or body cavity. The invention utilizes long flexible needles attached to sutures, which are passed through long flexible cannulas. The shape or path which the flexible cannulas form can be manipulated remotely by the operator such that they may be inserted into the surgical site in one configuration, such as relatively straight, and then a portion of the cannula can be warped or bent into another configuration once located within the targeted hollow organ or cavity.

Once the flexible cannulas are actuated to form the desired configuration at or near the surgical site, a suction capsule component or template can be introduced and incorporated with the configured flexible cannulas. The flexible cannulas can be aligned with corresponding receiving cannula incorporated within or about the suction capsule component. The suction capsule component may be in fluid communication with a vacuum source. The suction capsule component may also be contained by or be incorporated with an endoscope. The suction capsule component can be directed by the endoscope to the targeted tissue for suture incorporation. As the suction capsule is held adjacent to a targeted tissue, the vacuum may be activated drawing tissue into a suction opening of the capsule.

The long flexible needles are then advanced through the tissue held by the suction opening and continue up into the receiving cannulas. The needles are of such a length that they are at least as long as the collective distance of delivery cannula, the suction opening, and the receiving cannula. The long needles may be attached to suture such that two needles are attached to opposite ends of a length of suture. The suture is generally at least as long as the collective distance of the two needles. The suture may incorporate a graft. This graft may be delivered to the tissue distal to the incorporated tissue fold. A second or proximal graft may be incorporated with the sutures and slid into position proximal to the tissue and the first or distal graft. By securing the suture, the first or distal graft is anchored to the second or proximal graft, holding the incorporated tissue fold or folds between them. By delivering suture by the same means to opposing sides of an incision or defect, an incision or defect can be closed by securing the sutures. By alternating delivery and receiving functions of the cannula or cannula set, one can sew continually, incorporating multiple suture bites with one suture.

Figure 1:
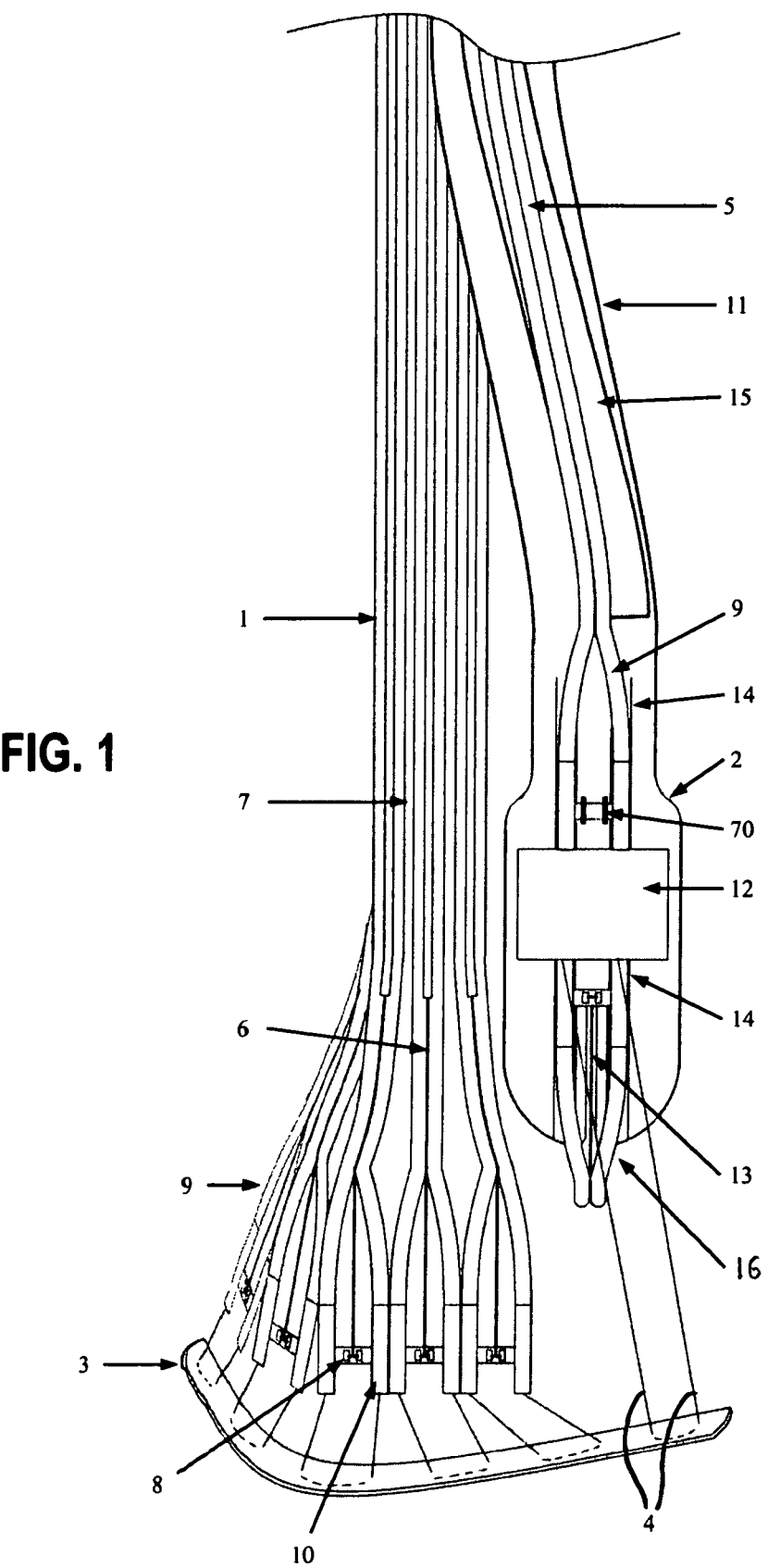
FIG. 1 illustrates a view of an exemplary embodiment of the present invention including delivery cannula sets, graft incorporated with sutures, and a suction component incorporated with a looped delivery cannula and a receiving cannula set.

FIG. 1 illustrates an exemplary endoscopic suturing and implant device 100 according to the present invention.

As illustrated in the exemplary embodiment of FIG. 1, the device 100 may include a delivery cannula set 1, a suction capsule component 2, a graft 3, sutures 4 attached to needles 16 contained within the delivery cannula sets, and a receiving cannula set 5. The delivery cannulas sets 1 and the suction capsule 2 with attached tube 11 may be of a length that is sufficient to span at least the distance from their place of insertion to the targeted surgical location. For example, in gastrointestinal (GI) uses, the delivery cannula sets 1 and suction capsule 2 with attached tube 11 can be approximately 2 to 3 feet. This length enables the components to reach several organs within the GI tract or within the abdominal cavity while their proximal ends remain outside the patient's body and accessible by an operator.

Figure 2:
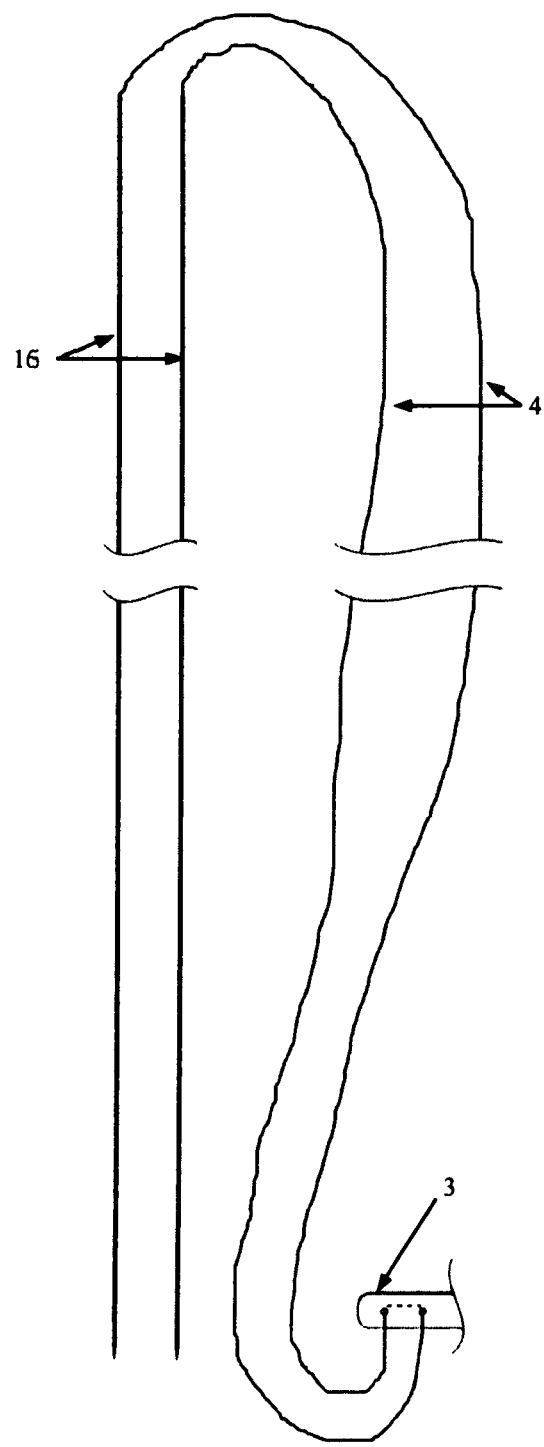
FIG. 2 illustrates a view of two long flexible needles attached to one suture which is incorporated into a graft.

As illustrated in FIG. 2, the device 100 may utilize long suture needles 16 made of a material that has the properties of shape memory, such as Nitinol. Nitinol is a nickel and titanium alloy that quickly returns to an original configuration after being flexed. Other materials may also be used, such as stainless steel, nylon, and plastic. The suture needles 16 can be of adequate length to reach a suturing site, via a natural body orifice such as the mouth or anus, or an incision or stoma, and return back out of the device. As such, the needles 16 may typically be at least twice the length of the delivery cannula set 1 of the device. As an example, a needle 16, utilized for GI applications, can be approximately 4 to 6 feet long. Each needle 16 can be attached to suture 4 to deliver and incorporate suture material into tissue that the needle 16 traverses.

As illustrated in FIG. 2, in one embodiment of the present invention, the needle 16 may be straight. The needle may have a flexibility to follow the path created by a cannula 1, which may include various turns and loops without the needle losing its original shape. The straight shape of the needle allows it to exit a cannula 1, transect a tissue drawn into and held by a suction port 12 or ports of a suction capsule component 2, and proceed in the direction in which it has been directed.

Needle 16 can be longer or shorter depending on the desired application, such as cardiac, vascular, gynecological, proctologic, pulmonary, and general surgical procedures. Needle 16 may have a distal tip or end that is made of a material that is more rigid, such as steel or titanium. The needles may have differing diameter or gauge depending upon the application. Possible diameters may range from about 0.012 inches to about 0.055 inches. A diameter of approximately 0.024 inches works well for GI applications. Needle 16 may also have an original configuration other than straight, such as having a bend, curve or coil. The elongated needle 16 may also have a detachable tip, with the detachable tip being attached to suture and the elongated shaft or wire serving as a pushrod.

Suture 4 attached to needle 16 may be made of any of the standard and common suture materials, including natural and synthetic, monofilament and multifilament, absorbable and non-absorbable materials. As illustrated in FIG. 2, each end of one length of suture 4 may be attached to a needle 16, creating what is known as a double-armed suture. Suture 4 may be attached to needle 16 in a standard fashion, with a drilled hole in the end of needle 16 and the suture 4 held within. Alternatively, a micro lumen tube (not shown) may be slid onto the corresponding ends of the needle 16 and suture 4 and bonded, thereby connecting suture 4 to needle 16. The micro lumen tube may be made of Polyimide tubing.

As illustrated in FIG. 2, the double-armed suture may be able to have each needle 16 pass through a graft, thereby incorporating the graft on a loop of suture 4.

Generally, a cannula is a tubular passageway though which material can travel in either a forward or backward direction. Cannulas 1 of the present device can have an internal diameter adequate to contain one or more needles 16 and accompanying sutures 4. Cannulas 1 are utilized to direct needle 16 to an intended point of incorporation with tissue. Cannulas 1 also direct the force necessary to maintain needle 16 in a forward or backward direction and contain or prohibit lateral movement and unintended bending of the needle 16.

Figure 3:
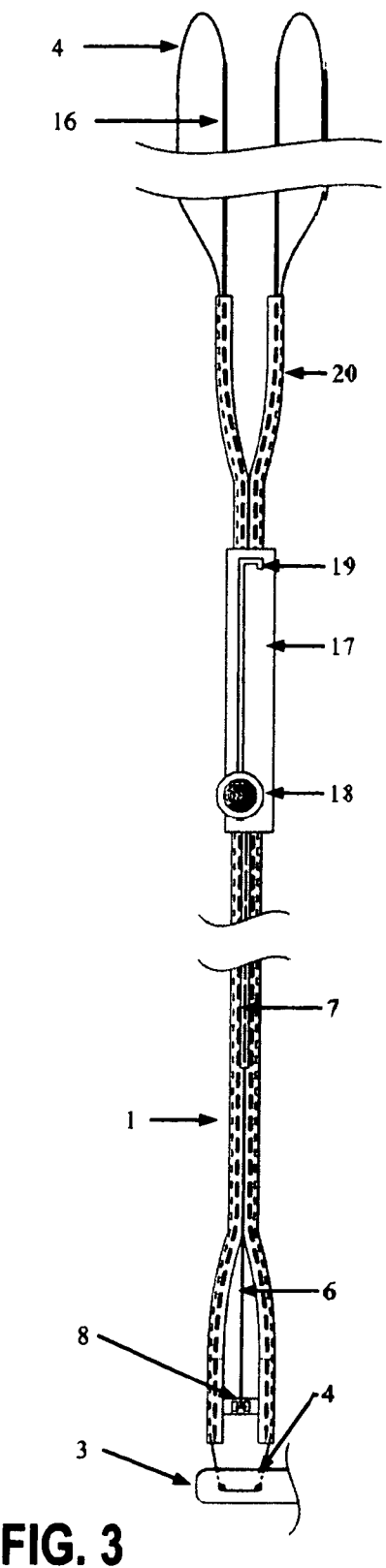
FIG. 3 illustrates a view of a delivery cannula set loaded with a double armed suture and incorporated graft.

As illustrated in FIG. 3, the delivery cannula set can be made up of two cannulas 1 joined together side by side. Each individual cannula 1 may have an internal lumen with a diameter of sufficient size to accommodate a needle 16 and attached suture 4, which at times may run side by side within an individual cannula 1. This diameter size may range from approximately one half millimeter to approximately two millimeters. The distal end of the cannula set may be configured such that each cannula 1 is held at a specific distance from one another. This space may be maintained by a connecting length of material 8, creating a forked distal end 9 of the delivery cannula set 1.

FIGS. 4A-4D illustrate front and side views of the set of delivery cannulas 1. The set of delivery cannulas 1 may contain or be connected to a third cannula or lumen 7 running parallel to the delivery cannulas 1 that contains a control or warping cable 6. Warping cable 6 may by made of wire or string. Warping cable 6 may be attached to the distal end of the set of delivery cannulas 1 at the cable attachment 8. Warping cable 6 is able to be pulled or pushed through the warping cable cannula or lumen 7 by raising or lowering the warping cable control lever 18 which is attached to the proximal end of the warping cable 6. Pulling the warping cable 6 may shorten the distance of the exposed cable between the distal end of the warping cable lumen 7 and the cable attachment 8 at the distal end of the delivery cannula set 10. This shortening of the exposed warping cable 6 pulls the distal end of the delivery cannula set 10 toward the end or the warping cable lumen 7, thereby warping or bending the cannula 1 and creating a loop 61 as illustrated further in FIGS. 4C and 4D. The warping cable control lever 18 may be maintained in position with the distal cannula ends 10 in the warped configuration 61 by moving the lever 18 to a catch 19 in the warping cable control compartment 17. The needles 16 with attached sutures 4 may be backed into the distal end 10 of the delivery cannula set 1 so that the needle tip or point is positioned at or near the distal end 10 of the delivery cannula set 1. The distal end of flexible needles 16 contained within the delivery cannula set 1 may be warped along with the distal end of the delivery cannula set 1. The cable attachment area 8 and or the distal end 10 of the delivery cannula set may be made of stainless steel or other material, which may be attracted by a magnetic force.

Warping cable 6 may be actuated in a variety of fashions. In one embodiment, the tension on the cable 6 is applied by rotating a spindle (not shown) in one direction or the other, having the cable 6 wrap around the spindle as it is rotates, thereby reeling in or shortening the cable's 6 length distal to the spindle.

In the embodiment illustrated in FIG. 1, needles 16 may be pushed by an operator through the delivery cannulas 1, down the length of the set of cannula 1, then directed upward at the bend 61 at the distal end of the set of cannulas 1. The needles 16 then pass out of the delivery cannulas 1 and traverse the area of the suction port 12 such that the needles 16 penetrate the tissue drawn into the bore of the suction capsule component 2 and held by the vacuum. The cannulas 1 may have flared or trumpet shaped openings 58 to assist in receiving the needle 16 once it has traversed the suction opening 12. The needles 16 may completely traverse the tissue held by the suction port 12, and may continue up the bore of the tube 11 or enter the receiving cannulas 5 at or near the upper side of the suction port 12. The attached sutures 4 that follow the needles 16 through the tissue are then incorporated into the tissue to create a bite or suture of tissue.

Cannula 1 can be flexible, but may optionally have rigid sections as necessary to allow turning and targeting of needles 16. Cannula 1 can be formed with one or more lumens. Cannulas 1 can be made of many materials. In one embodiment, cannula 1 or set of cannulas 1 sets can be made of extruded plastic tubing reinforced with braided stainless wire. Cannulas 1 may also be made out of, entirely or partially;

metal, Nylon, polytetrafluoroethylene, fluorinatedethylenepropylene perfluoroalkoxy, polyvinylidenefluoride, THV resin, ethylenetetrafluoroethylene, polyetheretherketone, and polyethylene.

FIGS. 5A through 5C illustrate a multi-directional warping cannula set 200. In this embodiment, there are one or two cannulas 1 for passing needles 16 and suture 4. Running parallel on opposing sides of this cannula 4 or cannulas 4 are two other cannulas or lumens 7 for housing the warping cables 6. By optionally pulling one warping cable 6 or the other 6, this cannula 1 or cannula set 200 has the ability to have its distal end warped from its straight configuration in two opposite directions within a plane. As described later, this is important in allowing continuous sewing with a double-armed suture within a space by eliminating the possibility of crossed sutures between bites.

A delivery cannula 1, set of, or series of cannulas 1 may also function as a receiving cannula 5, or a set of or series of receiving cannulas 5. The two may be interchangeable. What differentiates one from the other may be its position of incorporation with the suction capsule component 2, and its present function of either delivering or receiving needles 16. A delivery cannula 1 or a set or series of delivery cannulas 1 may be loaded with needles 16 and suture 4 and may be incorporated with a suction capsule component 2 such that the distal tip 10 of the cannula 1 is positioned distal to the suction opening 12 of the suction capsule component 2. One or more receiving cannulas 5 may be incorporated with a suction capsule component 2 such that its distal tips 10 are positioned proximal to the suction opening 12.

A set of delivery cannulas 1 and corresponding receiving cannulas 5 can be inserted into the patient in a variety of ways. The small diameter or cross section of the cannula sets 1 and 5 enables them to be inserted individually, as a group or series of cannula sets 1 and 5, and or previously incorporated with a suction capsule component 2. When inserted individually, the distal end of the cannula sets 1 and 5 may be configured in either a straight configuration or a warped configuration 61. A distal end configured with a looped distal end may produce an atraumatic distal end and limit the potential of traumatizing the tissue passed en route to the suturing target. Once in the targeted hollow organ or body cavity, cannula sets 1 and 5 may be reconfigured to the desired configuration.

Figure 6A:
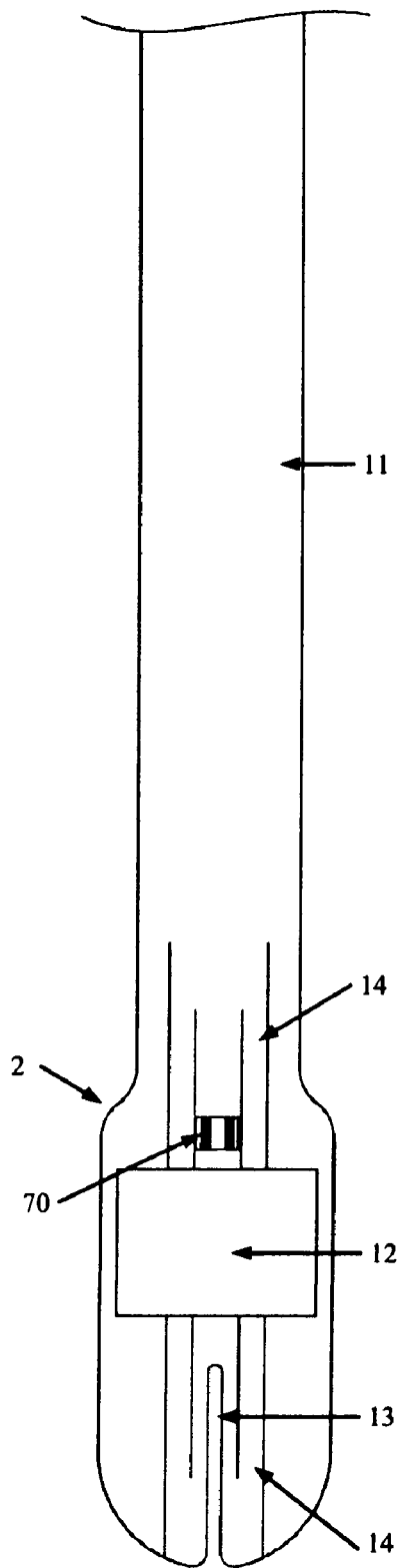
FIG. 6A illustrates a front view of a suction capsule component.
Figure 6B:
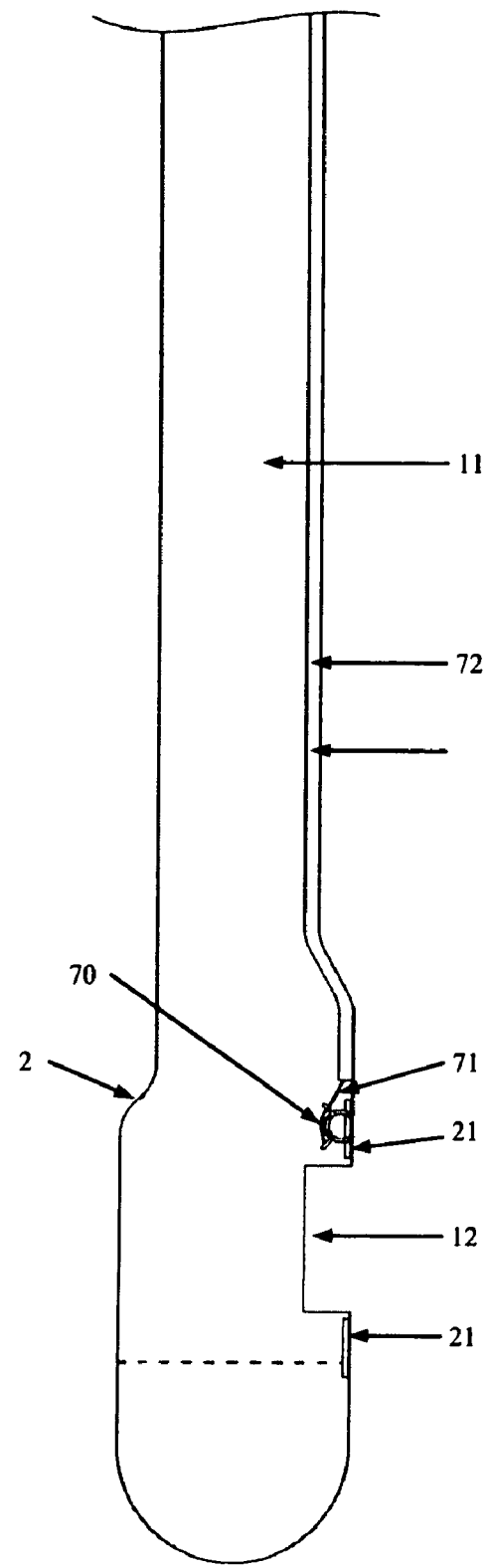
FIG. 6B illustrates a side view of a suction capsule component.

FIGS. 6A and 6B illustrate front and side views of a suction capsule component 2 embodiment that is formed with or connected to a tubular structure 11. The tubular structure 11, which may be hollow, may be made of a flexible plastic that may be transparent, translucent, or opaque. Tubular structure 11 may house an endoscope 15. Tubular structure 11 may include and be connected to the endoscope 15, or the endoscope 15 may work in concert with suction capsule component 2. Suction capsule component 2 may also work without an endoscope 15. Tubular structure 11 may be of sufficient length to have its proximal end extend from outside of the patient, while the distal end, which includes the suction capsule component 2, can reach organs and tissues within the patient's abdomen and thorax. Tubular structure 11 may be two to three feet. The diameter of the suction capsule component 2 may be of a size that is amiable for inserting into a natural body orifice, such as the mouth or anus. The diameter may range from about 5 mm to about 22 mm for oral insertion and about 5 mm to about 35 mm for anal and vaginal insertion. A diameter of approximately 14 mm may work particularly well for suturing procedures within the stomach. Tubular structure 11 connecting the suction capsule component 2 to the vacuum source may be of the same diameter as the suction capsule component 2, or it may be smaller. The diameter of tubular structure 11 may be from 2 mm to 35 mm.

The suction capsule component 2 and tube 11 may be in fluid communication with a vacuum source and can include one or more suction ports 12. Suction port 12 may be located near the distal end of tubular structure 11, although other locations are possible. Suction port 12 can completely or partially circumscribe a portion of suction capsule component 2. The area immediately distal and proximal to, and including, the suction port 12 may have the capability to expand and contract its diameter. Suction port 12 may be designed to draw tissue into the bore of the suction capsule component 2 when a vacuum is applied to tubular structure 11 with attached suction capsule component 2.

As illustrated in FIG. 6A, suction capsule component 2 may be formed such that there is a slot 13 in its distal end running substantially perpendicular to the midpoint of suction opening's 12 lateral length. Slot 13 may be formed by the outer surface of the suction capsule component 2. Slot 13 functions as a female receiving slot for warping cable 6 of delivery cannula set 1 when warping cable 6 has been engaged and the distal end of the delivery cannula set is in looped configuration 61, as illustrated in FIGS. 7B & 7C. The width of slot 13 may be wider at the distal end of the capsule 2 and taper to a narrower width at its apex. The top or apex of the slot 13 may have a width sufficient to contain warping cable 6.

In this embodiment, the area proximal and distal to the suction port 12 may have a plurality of vertical grooves 14 that are complimentary to receive the vertically running distal ends of the delivery cannula set 10 and the receiving cannula set 10. Magnets 21 may be positioned within the bore of suction capsule component 2, or within the wall of the suction capsule component 2, corresponding to the location where the distal end 10 of the cannulas sets 1 & 5 are intended to be positioned when the capsule is armed for suture deployment. The magnets 21 may draw and help to hold the distal end 10 of the cannula sets 1 & 5 in the proper configuration for suture deployment. The device may have a catch 70 that can be actuated remotely to further releasably secure the receiving cannula set 5 distal end 10 in position above the suction port 12 during suture deployment. Catch 70 may be actuated by using a cable 71 within a lumen 72 contained within and running up the suction capsule component 2 and the attached tube 11, as illustrated in FIG. 6B. In one embodiment, a receiving cannula set 5 is not utilized, as the wall of the suction capsule component 2 proximal to the suction port 12 is configured to receive the needles 16 within the suction capsule component, allowing the needles 16 to proceed up inside the bore of the tubular structure 11 of the device. The distance the magnet 21 is held from the interior wall of the suction capsule component 2 may be able to be remotely altered, thereby increasing or decreasing the intensity of the magnet's 21 pull on the distal cannula 10.

Generally, an operator manipulates tubular structure 11 to place the suction capsule component 2 to the desired location. The endoscope 15 contained within the tubular structure 11 of the device may direct the device to its target by applying force to the interior wall of tubular structure 11, thereby steering the device in the direction in which the force is applied. Suction capsule component 2 may be attached to the distal end of the endoscope 15 with tubular structure 11 either running up one of the endoscope's working channels, or tubular structure may run along the side of endoscope 15. Alternatively, tubular structure 11 may have the ability to direct or steer itself by using various methods of steering. For example, a balloon catheter (not shown) can run parallel within or along a side of tubular structure 11. The catheter may be endoscopically placed in a defect, annulus, valve, or outlet, and inflated to hold the device in place. Tubular structure 11 can then be slid down the catheter to be positioned and maintained in the desired location. Tubular structure 11 can incorporate radio opaque markers (not shown) to enable visualization using fluoroscopy. In yet another variation, wires or cables can be used by varying tensions to turn the device within the closed organ or space.

As illustrated in FIGS. 7A-C, suction capsule component 2 may be designed to receive the looped portion 61 of the delivery cannula set 1 such that warping wire 6 slides into and fits securely within slot 13 at the distal end of the suction capsule component 2. Suction capsule component 2 may be able to be maneuvered within a body cavity, enabling these two units, the suction capsule component 2 & the delivery cannula set, to be coupled within a body cavity. Once suction capsule component 2 is coupled with the cannula sets 1 & 5, the unit is armed and ready to deploy the needle(s) and attached suture.

Figure 8:
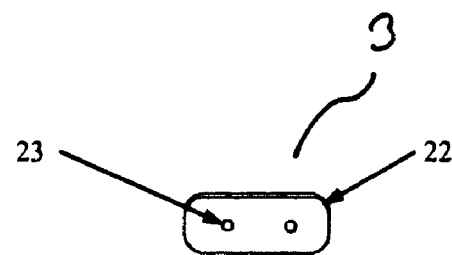
FIG. 8 illustrates a view of a pledget.

FIG. 8 illustrates an exemplary graft 22a, which may be a pledget. This graft or pledget 3 may have suture material 4 looped through the body of the pledget. The graft 3 may have existing holes 23 to accommodate the passing of suture material 4 through it, or alternatively, the graft 3 may have no holes, and the needles with attached sutures are simply passed through the material 22 of graft 3 via the penetration of the needle's sharpened point. The function of graft or pledget 3 may be similar to that of a washer on a bolt, in that it bolsters the suture's fixation in tissue and serves as and anchor, providing a larger surface area and reducing the ability of the suture material to tear out of the tissue. Grafts or pledgets 3 can be placed on the distal side of a suture bite as well as on the proximal side of a suture bite.

Figure 9:
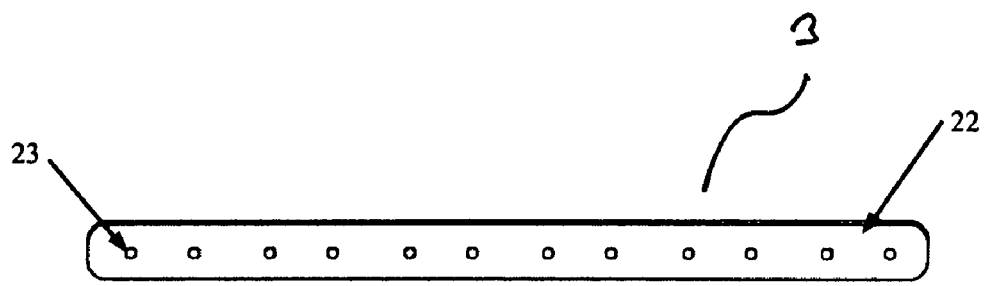
FIG. 9 illustrates a view of a linear graft.

FIG. 9 illustrates a linear graft 3 which functions similarly to the pledget 3 described above, though the added length enables multiple sutures to be incorporated, which in turn enables multiple bites of tissue to be incorporated and fixed in multiple configurations. Linear graft 3 can be rigid, flexible, or flaccid. Linear graft 3 can be fixed with suture to tissue by having a loop of suture run through two points of incorporation with the grafts 3 and then having the two resulting suture arms each run through two points of incorporation with tissue and then having the suture arms proximal to the tissue tied or secured. Linear graft 3 can also be fixed or secured to a second graft with tissue incorporated in between the two grafts. This can be accomplished by incorporating a second graft with the suture arms after the first graft 3 has been incorporated with tissue and prior to tying or securing them. Then the suture arms are tied or secured.

Linear graft or grafts 3 can be incorporated with tissue and secured to form a straight, curved, irregular, or circular configuration.

Figure 10:
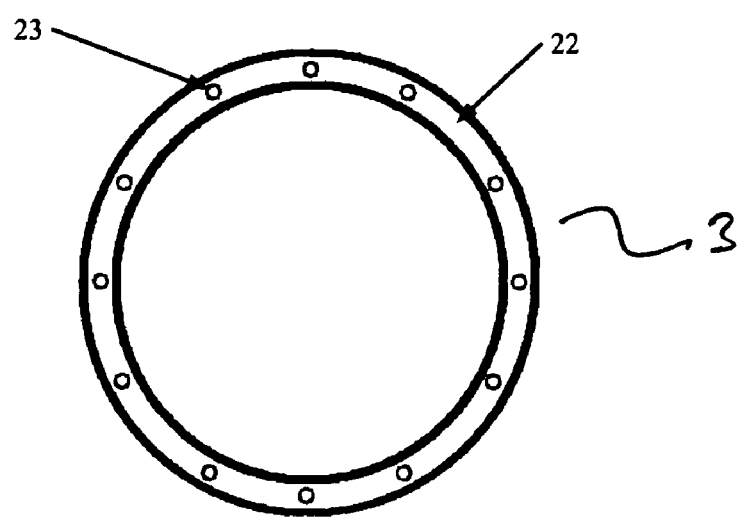
FIG. 10 illustrates a view of a circular graft.

FIG. 10 illustrates a graft 3 that is formed as a closed circle. This circular configuration can be useful for securing tissue about its circumference to create a restrictive outlet or orifice. This configuration of graft 3 can be made of the same materials as the pledget and linear graft, such as plastic, silicone, polypropylene, Nitinol, stainless steel cable, Gortex, Nylon, Teflon, fabric, rubber, cotton, stainless steel, Nitinol, titanium, carbon fiber, composites of material, or another like material which is compatible with biologic tissue.

Graft 3 may be made of a biodegradable or absorbable material such that it is designed to degrade in integrity over time, allowing for the effects of the graft to be temporary. Graft 3 may be coated with, contain within, or be made of an agent that is eluded from the graft in a designed dosage over time. This agent could be a drug such as a hormone or steroid therapy, an appetite suppressant, an anti-inflammatory, an antibacterial agent, a hemostatic agent, a bio-adhesive, a birth control, etc.

Figure 11:
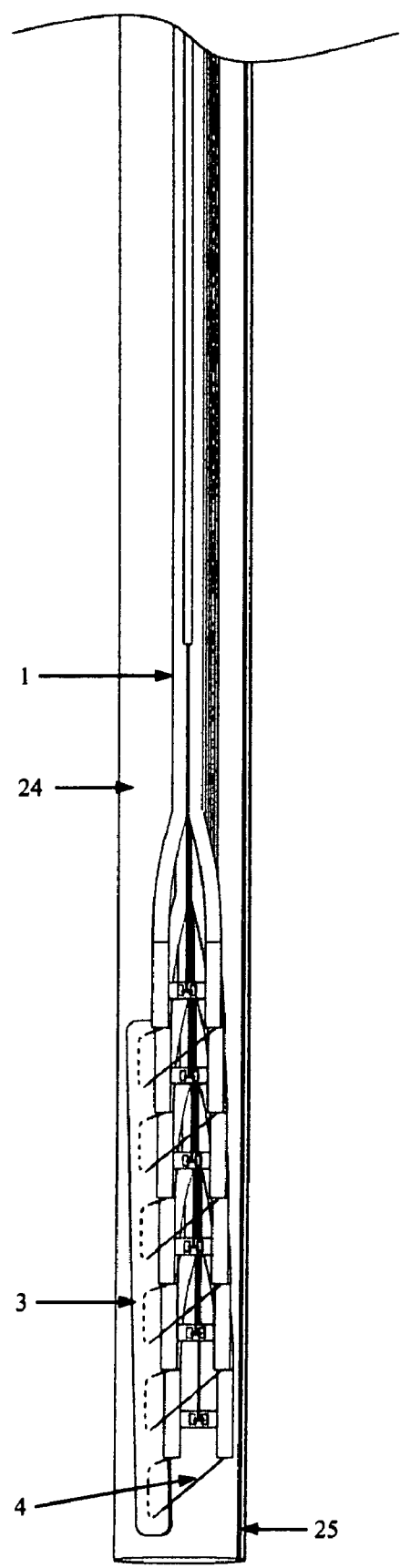
FIG. 11 illustrates a view of a series of delivery cannula sets loaded with double-armed sutures which are incorporated into a linear graft, all of which are covered by a removable tubular sheath.
Figures 32A, 32B:
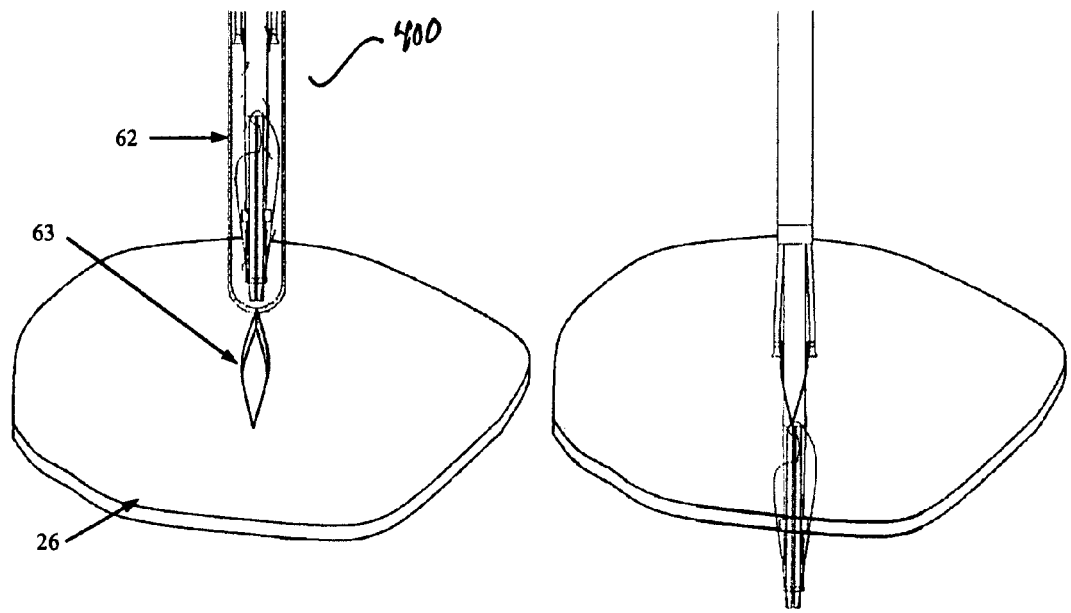
FIG. 32A illustrates a view of an embodiment of the invention covered by a plastic sheath prior to insertion through an incision or defect.
FIG. 32B illustrates a view of an embodiment of the invention with delivery cannula tips passed through an incision or defect.

FIG. 11 illustrates delivery cannula sets 1 loaded with double-armed sutures 16, 4 incorporating a linear graft 3 and covered or encased by a removable tubular sheath 24. Removable sheath 24 may be useful in assisting in the insertion of the cannula sets 1 & 5 and accompanying graft 3 by containing the components within a limited diameter tube and by covering the distal tips 10 of the cannula sets 1 & 5 which could cause trauma to tissue during insertion. Removable sheath 24 may have a slit 25 running the length of the sheath 24, enabling it to be removed from the cannula sets 1 & 5 as it is withdrawn from the patient without having to pull it over the proximal ends of the cannula sets 1 & 5. Depending upon the number of delivery cannula sets 1 utilized, the size of the graft 3, and the orifice used for insertion, the diameter of sheath 24 utilized may vary from about 5 mm to about 35 mm. Alternatively, a thin plastic sheath or bag (not shown) may be used to contain the components and smooth their insertion into a natural orifice or small surgical incision. A similar sheath is illustrated in FIG. 32A. The distal ends of the components may simply be pushed through the material of the thin plastic sheath or bag once the components were positioned in their targeted location. Sheath 24 or bag may be easily removed from the device components by ripping or tearing the material off of the device components.

Figure 12A:
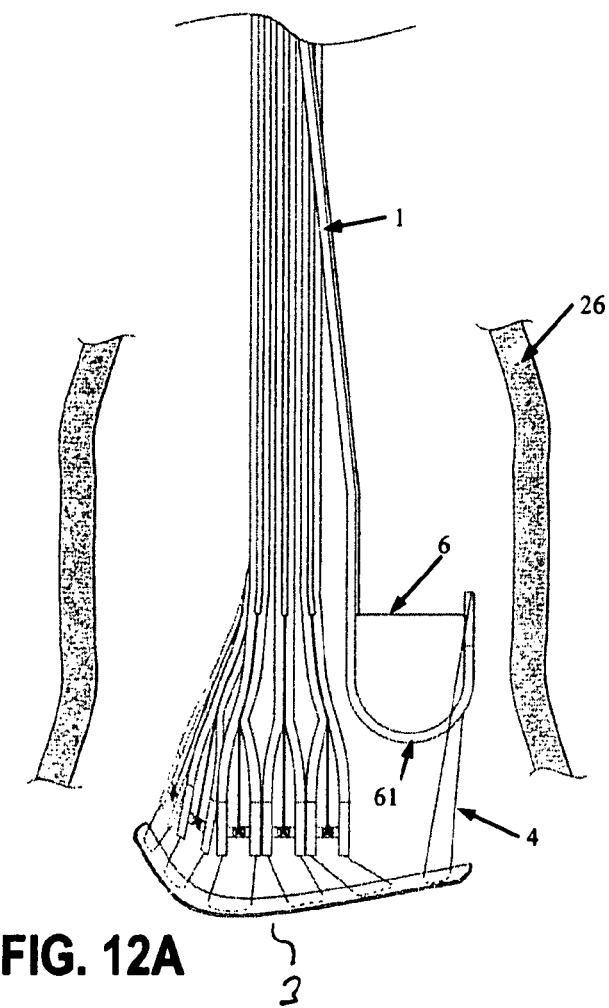
FIG. 12A illustrates a view of a series of delivery cannula sets loaded with double-armed sutures and graft inside a hollow organ with one delivery cannula set warped and ready to receive a suction capsule component.

FIG. 12A illustrates a series of delivery cannula sets 1 loaded with double-armed sutures 4 with incorporated graft 3 positioned within a hollow organ or body cavity. In this embodiment, each double-armed suture is intended to be delivered and incorporated with tissue individually, one set at a time. As demonstrated in FIG. 12A, one delivery cannula 1 has been warped, creating a looped distal end 61, and is ready to receive or fit into a suction capsule component 2. When the distal end of the delivery cannula set 1 is warped, additional suture 4 slack may by formed between the distal end 10 of the delivery cannula set 1 and the graft 3.

Figure 12B:
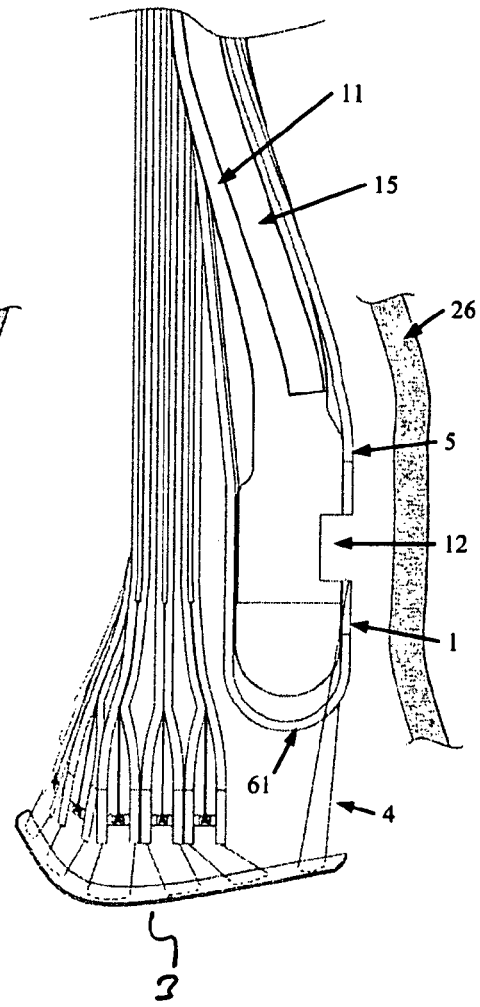
FIG. 12B illustrates a view of a series of delivery cannula sets loaded with double-armed sutures and graft inside a hollow organ with one delivery cannula set warped and incorporated with a suction capsule component.

The suction capsule component 2 and attached tubular structure 11 may be introduced or inserted into the intended suturing site by itself as an individual unit, independent from the delivery cannula set or sets 1. FIG. 12B illustrates a delivery cannula set 1 coupled or temporarily held by the suction capsule component 2. In this embodiment, the suction capsule component 2 utilizes receiving cannula sets 5 that are releasably held in place proximal to the suction opening 12. The warped delivery cannula set 1 is held in its proper position in relation to the suction capsule component by the tension the warping cable 6 creates between the cannula loop 61 and suction capsule component 2. The grooves 14 within the suction capsule component 2 may enable the distal ends of the delivery cannula set 1 to lie precisely in their intended position below the suction opening 12. In this embodiment, the endoscope 15 contained within tubular structure 11 is able to move and navigate the suture capsule component 2 directing the suction capsule component's suction opening 12 adjacent to the tissue 26 intended for suture incorporation.

Figure 13A:
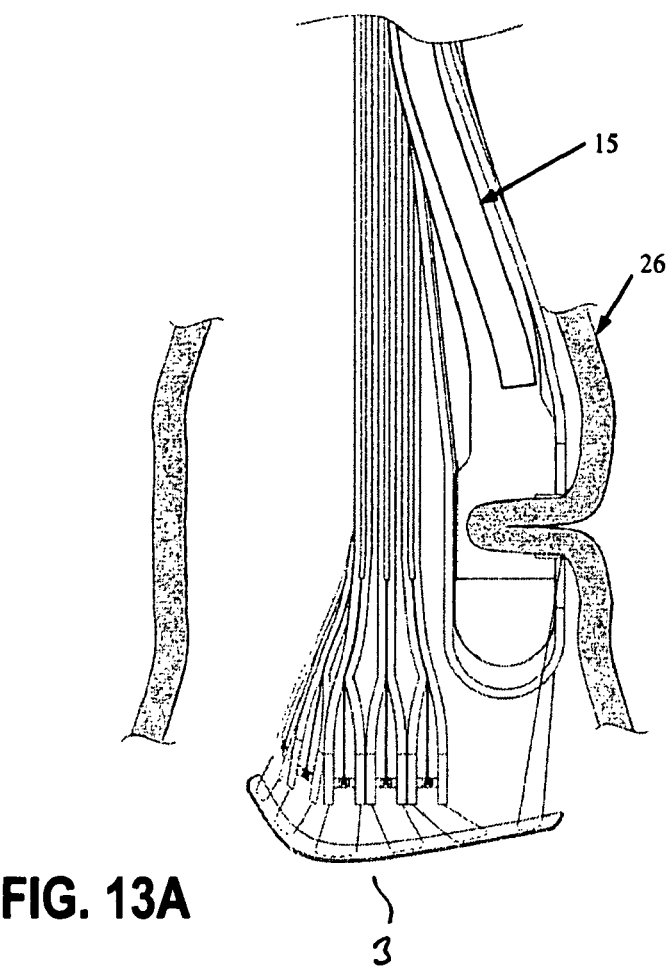
FIG. 13A illustrates a view of a series of delivery cannula sets loaded with double-armed sutures and graft inside a hollow organ with one delivery cannula set warped and incorporated with a suction capsule component which has tissue drawn into its suction opening.

The suction capsule component 2 and attached tubular structure 11 may be in fluid communication with a vacuum source. As illustrated in FIG. 13A, when the vacuum is activated, negative pressure draws the tissue adjacent to the suction opening 12 into the bore of the suction capsule component 2. The needles 16 with attached sutures 4 contained within the warped delivery cannula set 1 may now be advanced through the delivery cannula set 1 and across the suction opening 12, penetrating and traversing the tissue 26 drawn into and held by the suction opening 12. In this embodiment, needles 16 enter a receiving cannula set 5 after traversing the suction opening 12. Once the distal ends of the needles 16 emerge out of the proximal end of the receiving cannula set 5, they may be grasped and pulled completely out of the receiving cannula set 5 drawing the attached suture through the tissue.

Figure 13B:
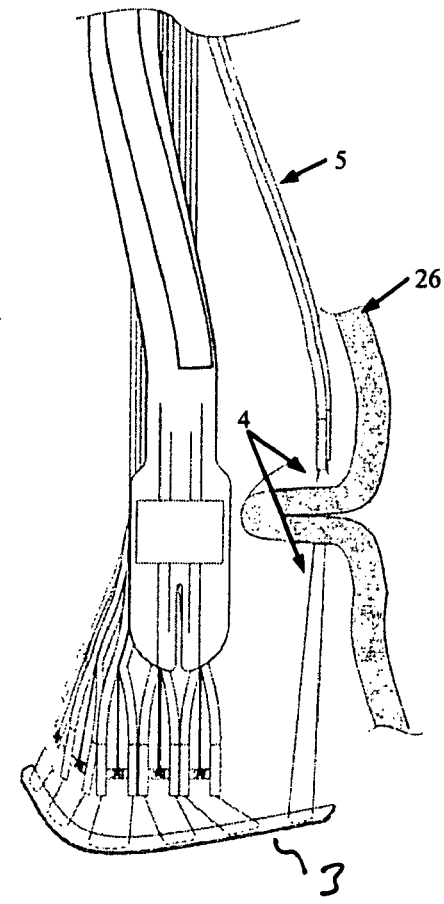
FIG. 13B illustrates a view of a series of delivery cannula sets loaded with double-armed sutures and graft inside a hollow organ with one set of sutures deployed into the drawn-in tissue.

As illustrated in FIG. 13B, after passing a double-armed suture 1, 4 through the tissue 26, the receiving cannula set 5 can be disengaged from the suction capsule component 2, leaving receiving cannula set 5 in place. Leaving receiving cannula set 5 in place serves to maintain the implanted double-armed suture's suture arms in order within the receiving cannula set's lumens. Instead of strands of flaccid suture material 4 running up a patient's esophagus, or other tubular organ, which may need to be maintained in proper order, the strands are held within the more easily manageable cannulas 1 and 5. The delivery cannula set 1 that had just delivered the back-loaded double-armed suture 1, 4 is now empty and may be disengaged from the suction capsule component 2 and removed from the suturing site. Suction capsule component 2 is now available to be coupled with a subsequent delivery cannula set 1.

Figure 14A:
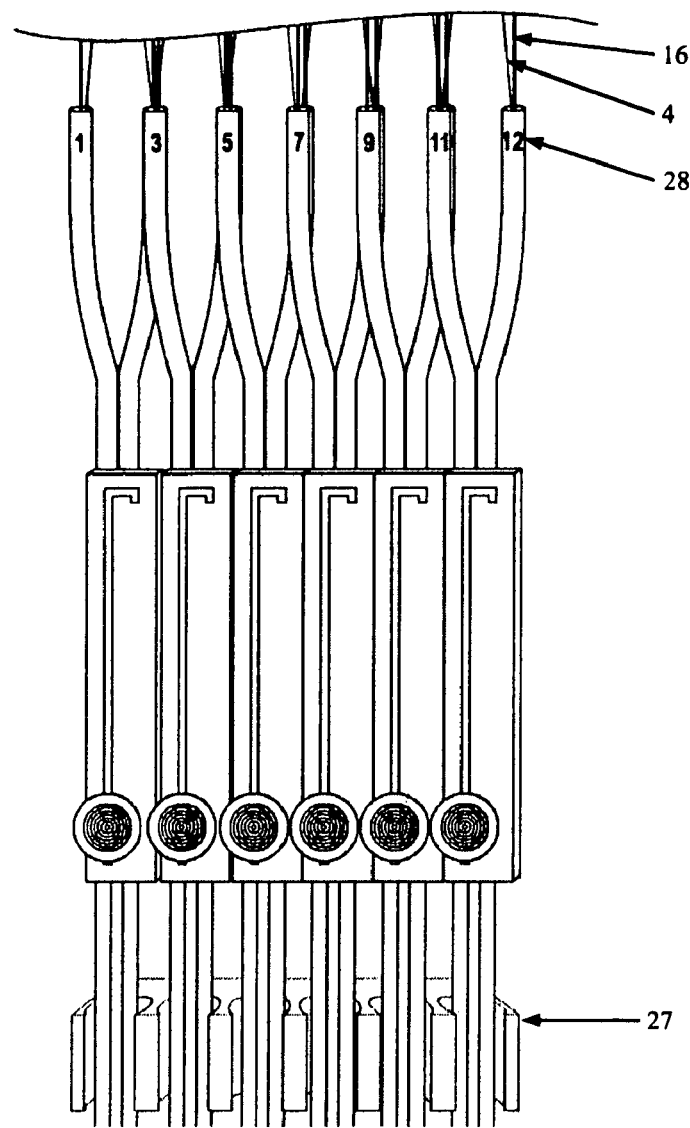
FIG. 14A illustrates a view of the proximal ends of a series of delivery cannula sets held by a linear organizing component.
Figure 14B:
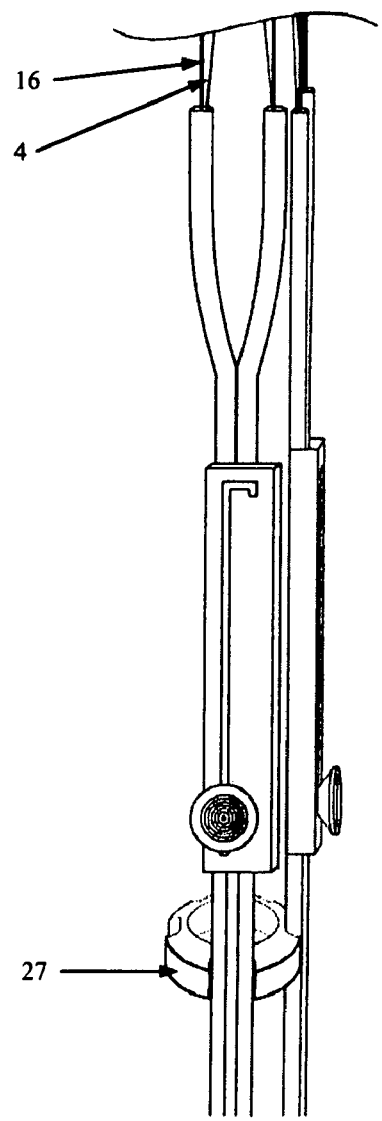
FIG. 14B illustrates a view of the proximal ends of a series of delivery cannula sets held by a circular organizing component.

FIGS. 14A & 14B illustrate how the proximal ends of the delivery and or receiving cannula, cannula sets, or cannula series 1 and 5 may be organized and maintained outside of the patient. A holder 27 designed to releasably hold at least one cannula, cannula set, or cannula series 1 and 5 may be formed in several configurations. Holder 27 designed to hold and maintain cannulas in a linear fashion is demonstrated in FIG. 14A. Holder 27 may have a series of cavities or grooves designed to releasable hold at least one cannula, cannula set, or cannula series 1 and 5. Holder 27 illustrated in FIG. 14B is designed to releasably hold at least one cannula, cannula set, or cannula series 1 and 5 in a circular fashion. The circular cannula set holder 27 may have a hole in its center allowing the tubular structure 11 of the suction capsule component 2 to be passed through it. Maintaining cannulas 1 and/or 5 in an organized fashion facilitates the proper orientation for incorporation of the contained sutures 4 with a proximal graft (not shown) or grafts and facilitates the proper orientation for securing of the suture arms 4. As illustrated in FIG. 14A, the distal, and or proximal, end of the cannula sets 1 and 5 may have numbers, colors, or codes 28 to help identify each individual cannula and cannula set or series 1 and 5. Holder 27 may be held by hand or be mounted to a table, stand, endoscope 15, or to tubular structure 11 of the device.

Figure 15:
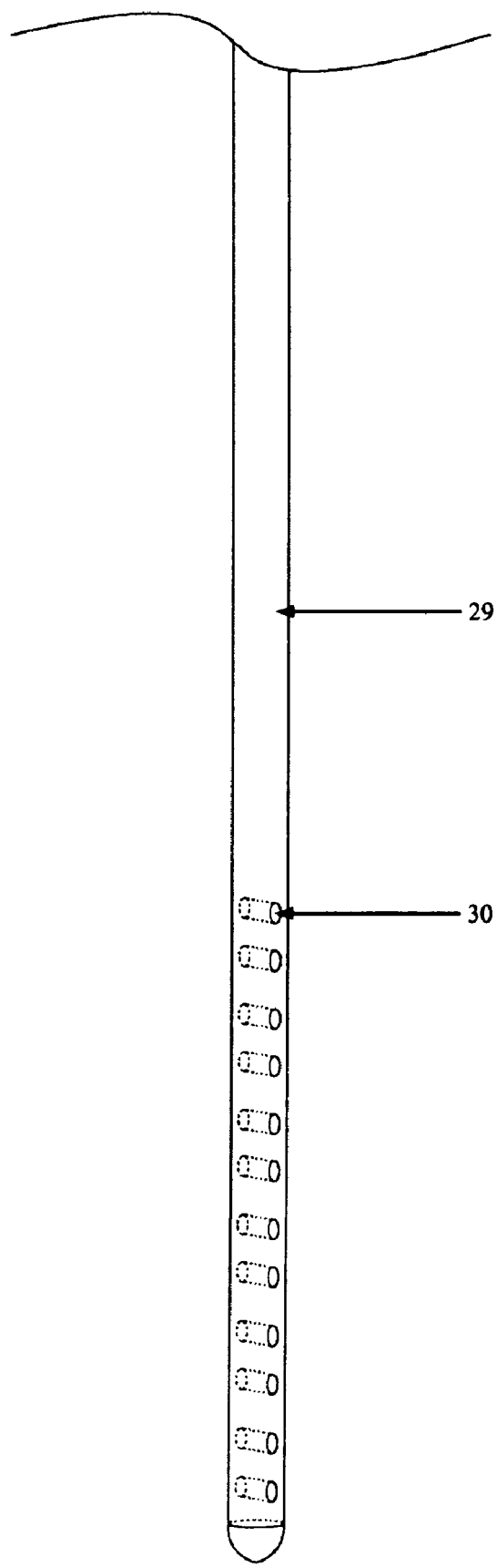
FIG. 15 illustrates a view of a graft pusher.
Figure 16A:
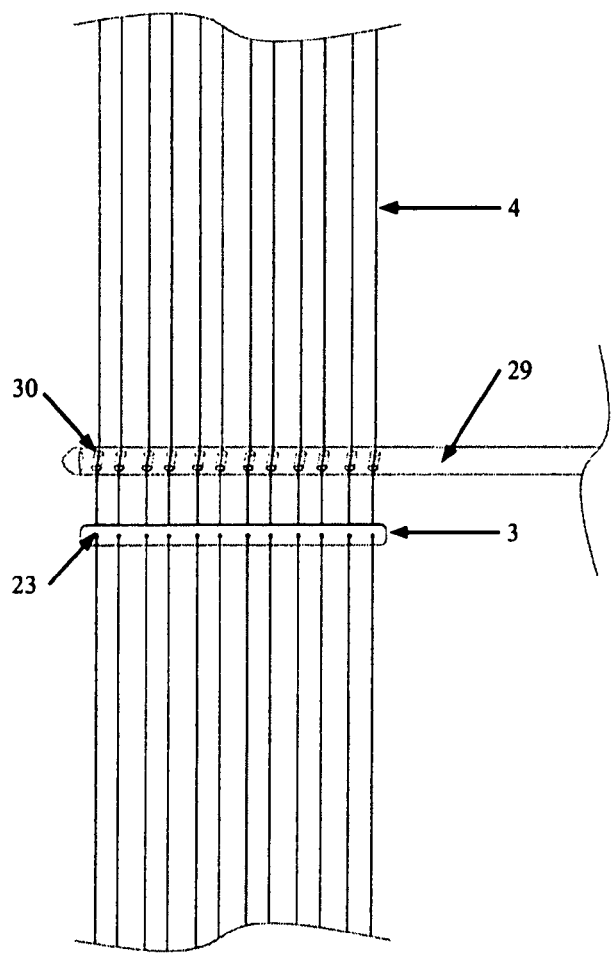
FIG. 16A illustrates a view of a series of sutures incorporated with a graft pusher and a graft positioned perpendicular to the sutures.
Figure 16B:
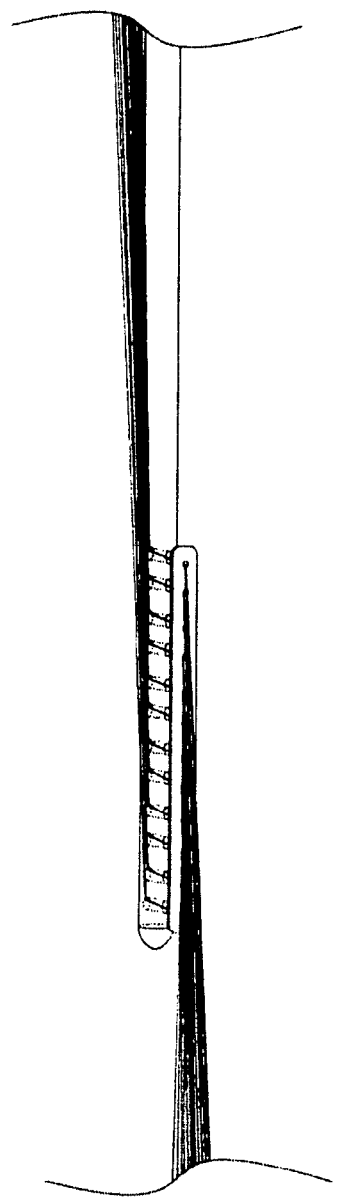
FIG. 16B illustrates a view of a series of sutures incorporated with a graft pusher and a graft positioned parallel to the sutures.

FIG. 15 illustrates an endoscopic graft pusher 29 used as a component of the implant system for introducing proximal grafts (not shown) into an internal suturing site. The graft pusher 29 may be a semi-rigid flexible rod that is of a length sufficient to extend from outside of a patients body into an internal organ or body cavity such as the stomach or peritoneal cavity via a natural body orifice or small surgical incision. For gastrointestinal applications, graft pusher rod 29 may be approximately 2 to 3 feet in length. The diameter of graft pusher 29 may vary, but generally its diameter may be from about 3 mm to about 10 mm. The proximal end of graft pusher 29 may be held by the operator. The distal end of graft pusher 29 may contain at least one hole 30 running completely through graft pusher's 29 material. The holes 30 are designed to allow suture 4 to pass through it. The holes 30 on the distal end of the graft pusher 29 may be spaced in a fashion that is complimentary to the spaces of suture incorporation holes 23 on a proximal graft 35 illustrated in FIG. 16A. The alignment of holes 30 & 23 reduces friction, which may be increased when the graft 35 and graft pusher 29 are advanced and holes 30 & 23 are not to be aligned. Once proximal graft 35 has been incorporated with the sutures 4 running up from their point of incorporation with tissue, graft pusher 29 is incorporated with the sutures 4 and slid down the suture material 4 until it comes in contact with proximal graft 35. Graft pusher 29 may now be rotated so that it is orientated such that is running parallel with the suture arms 4, as illustrated in FIG. 16B. With the suture arms held under tension, graft pusher 29 may be slid down the series of suture arms 4, advancing graft 35 down the suture arms 4 until graft 35 is within the intended hollow organ or body cavity. Graft pusher 29 can then simply be removed by pulling graft pusher 29 out of the patient the way it came in. Graft pusher 29 may be made of a variety of materials such as plastic, nylon, metal, Nitinol or a combination of materials.

Suturing device 100 is able to deploy sutures 4 about the circumference of the lumen of an organ such as the stomach with unsecured mattress suture bites. FIG. 17A illustrates a sectional view of a distal linear graft 3 having had all of its incorporated sutures 4 incorporated with bites or folds of tissue 32, and also having receiving cannula sets 5 in position above the incorporated tissue maintaining the order and organization of the suture arms 4 held within their lumens. The receiving cannula sets 5 may be removed individually so that the sutures 4 contained within may be secured or alternatively incorporated into a second of proximal graft 35. If a proximal or second graft 35 is incorporated, the receiving cannula sets 5 may be replaced back onto the sutures after the proximal or second graft 35 has been positioned within the suturing site by the graft pusher 29, and the graft pusher 29 has been withdrawn from the site and the sutures 4. This may be done to maintain order of the suture arms 4 as the receiving cannula sets may subsequently be removed one at a time and the suture arms tied or secured individually. FIG. 17B illustrates a proximal or second graft 35 secured to a distal or first graft 3 within a hollow organ or body cavity.

A secured mattress suture bite may be provided wherein the two arms of a suture 4 enter the first side of an object and/or tissue, exit a second side of an object and/or tissue, and are secured together, thereby forming a closed circuit of suture material 4.

The second or proximal graft 35 may be formed as a ring, as illustrated in FIG. 10, or it may be a length of material similar to the distal graft as illustrated in FIG. 9. If the distal and proximal grafts 3 and 35 utilized are linear lengths of material, they may be incorporated with the sutures 4 and aligned such that, when formed as a circle, the breaks in their circumferences 34 are not aligned with each other. In an exemplary embodiment, the breaks in the circumference 34 may be approximately 180 degrees apposed, as illustrated in FIG. 17B. The circumferential attachment of the two lengths of material 3 & 35 with their endpoints misaligned produces a circumferential fixation that may possess the strength of a hoop having no breaks.

The implantable grafts 3 & 35 (or rings) are used to hold or secure portions of the stomach's or organ's wall around their circumference. Graft 3 is illustrated in FIG. 17C. In one embodiment, two rings 3 and 35 are used to create a restricted outlet 33 within an organ. In another embodiment, only one closed circle ring 3 is used and the suture loop on the opposite side of the tissue can be bolstered through the use of individual pledgets (not shown). The rings 3 and 35 can serve as anchors for each other and for the sutures 4, which have been incorporated into the tissue wall 26, for example, as illustrated in FIGS. 17B, 17C, 18A &18B.

Figure 18A:
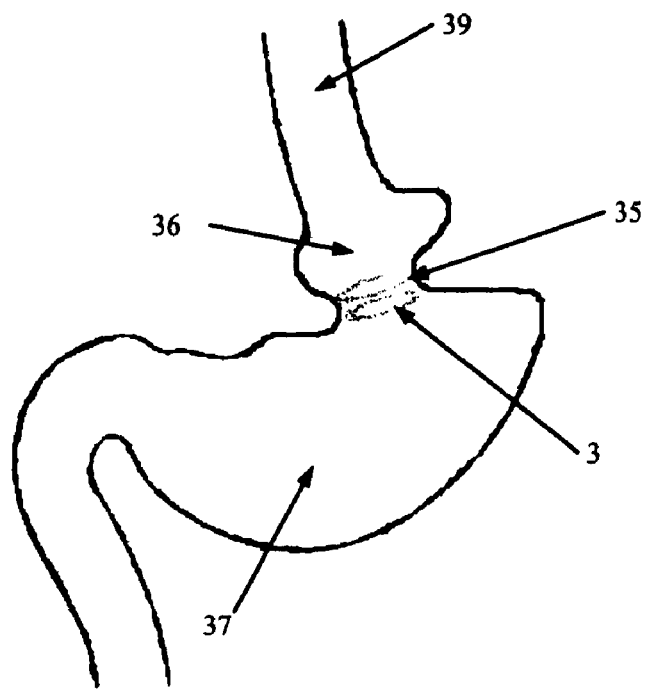
FIG. 18A illustrates a view of a stomach with the incorporated grafts forming a proximal stomach pouch with a limited volume.
Figure 18B:
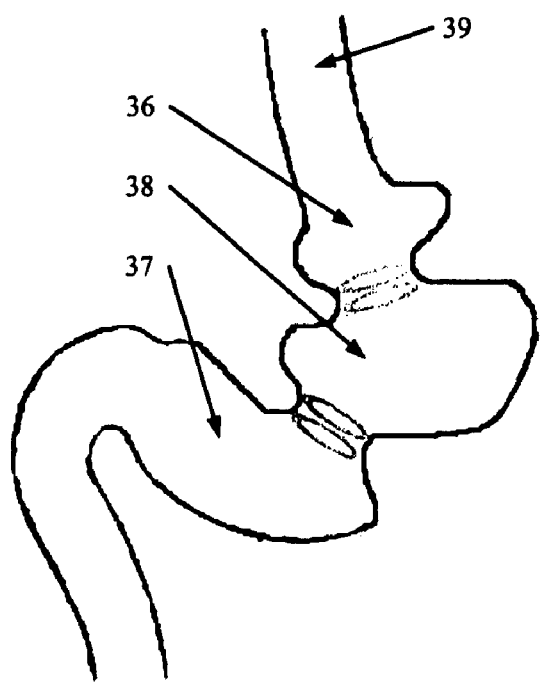
FIG. 18B illustrates a view of a stomach with the incorporated grafts forming a proximal, intermediate, and distal stomach pouches with limited volume.

FIGS. 18A & 18B illustrate the implantation of the graft 3, or grafts 3 and 35, and the creation of a gastric pouch 36. The size of gastric pouch 36 may vary in size. Surgeons often cite 15 cc to 50 cc to be the target volume size of pouch 36. The size of an outlet 33 created by the rings 3 and 35 may also vary in size. Surgeons often cite a 10 mm to 15 mm diameter as the target size for the outlet 33.

In the exemplary embodiment where distal and proximal grafts 3 and 35 are employed, once implanted, the result is two rings 3 and 35 held together with tissue sandwiched between them, as illustrated in FIG. 17B. In the stomach, because the diameter of the organ's lumen can be substantially larger that the diameter of the implanted grafts 3 and 35, the entire circumference of the organ may not be incorporated between the formed rings or grafts 3 and 35. Folds or pleats 32 from sections of the organ's circumference are held by the rings, similar to the configuration of a cinched sac or pleated curtain, as illustrated in FIG. 17C. The pliability of the tissue folds may serve to create a competent or near competent proximal gastric pouch 36.

The tissue 32 held between the grafts 3 and 35 may protrude within the circumference of the grafts 3 and 35. This produces a small outlet 33 whose orifice is made up of the tissue 32 of the organ. The size of the resulting outlet 33 can be measured and altered as necessary for the particular patient at the time of implantation by varying the amount of tension between the grafts and or by selecting a larger or smaller proximal graft 35.

As illustrated in FIG. 18B, multiple sets of rings or grafts can be implanted within a single organ. Implanting additional sets of rings may create additional outlets 33 and additional organ pouches 36, 37, 38. Additional outlets 33 and organ pouches 36, 37, 38 may further restrict the capability of the patient to intake food and may slow the patient's gastric emptying time, thereby increasing the effectiveness of the procedure. Additional grafts may also reduce the overall volume the organ is able to hold, just as a crushed can holds less fluid than a perfectly cylindrical can. Circular placed grafts 3 and 35 may also restrict the organ's ability to expand and stretch.

If necessary, a gastric ring graft implantation procedure can be easily reversed by simply cutting the sutures connecting the rings while using endoscopic instrumentation, and removing the grafts or rings 3 and 35.

FIGS. 19A-19F illustrate the suturing device sewing or suturing in a continuous fashion within a confined space. In this embodiment, the component nature of suturing device 100 may enable the operator to alternately switch the position and function of the delivery cannula set 1 with the receiving cannula set 5, and vice versa, in relation to its interaction with the suction capsule component 2.

Suturing device 100 may operate with cannula sets 1, 5 that have only one lumen for passing a needle 16 attached to suture 4, or it may operate with cannula sets 1, 5 that have more than one lumen for passing needles 16 attached to suture 4.

Suturing device 100 is able to sew tissue in multiple configurations by producing; mattress suture bites, pledgetted mattress suture bites, continuous running suture line, or continuous double running suture line. A description of a method for producing at least two suture bites with one double-armed suture within a hollow organ or body cavity follows. Other suturing configurations will become apparent to those skilled in the art.

Figure 19A:
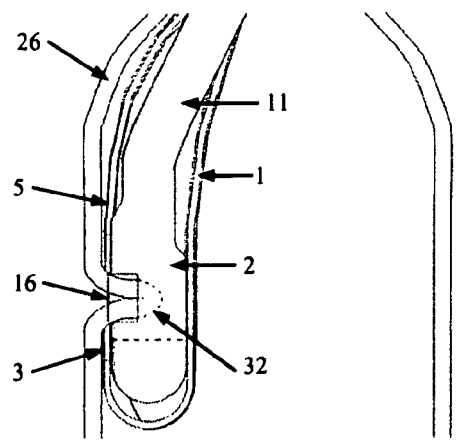
FIG. 19A illustrates a sectional view of the device components in use.

As illustrated in FIG. 19A, suturing device 100 may be introduced into a hollow organ or body cavity as a unit with delivery and receiving cannula sets 1, 5 releasably attached to the suction capsule component 2. Alternatively, the components may be inserted individually and coupled within the hollow organ or body cavity. The suction port 12 of the suction capsule component 2 is held adjacent to the tissue intended for suture incorporation. The vacuum is activated, drawing tissue into the bore of the suction capsule component 2.

The double-armed sutures with long flexible needles 16 are advanced through the delivery cannula set 1, crossing the suction opening 12, thereby penetrating and traversing the tissue fold created and held by the negative pressure of the suction opening 12.

After the needles 16 cross suction opening 12, they enter the releasably held receiving cannula set 5 and continue up the cannulas until they emerge out of the receiving cannula set's proximal ends. There needles 16 are grasped and pulled completely through. Receiving cannula set 5 is then released from suction capsule component 2 by actuating the receiving cannula catch 70.

Figure 19B:
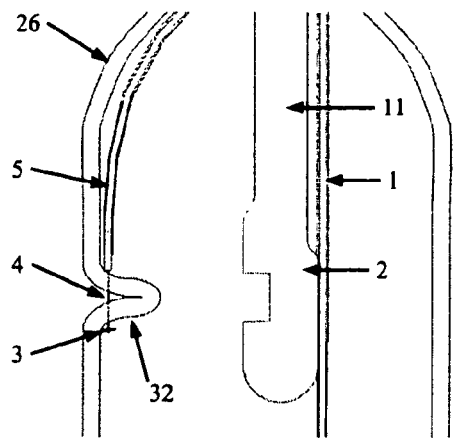
FIG. 19B illustrates a sectional view of the device components in use.

Referring to FIG. 19B, the initial delivery cannula 1 is now configured into a straight configuration by actuating warping cables 6 of cannula set 1, thereby disengaging the initial delivery cannula set 1 from suction capsule component 2.

Figure 19C:
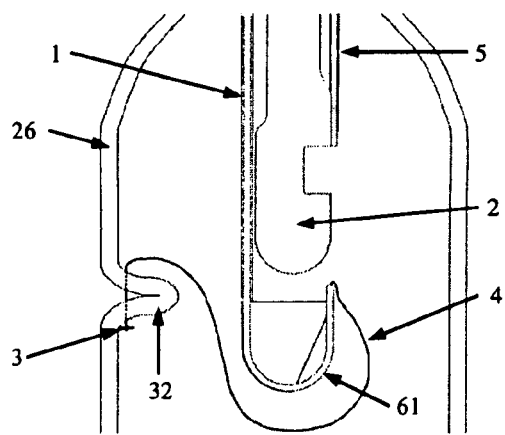
FIG. 19C illustrates a sectional view of the device components in use.

Referring to FIG. 19C, suction capsule component 2 is rotated or maneuvered so that the front of the capsule 2 is now positioned adjacent to the initial delivery cannula set 1. The initial delivery cannula set 1 and the suction capsule component 2 are aligned such that the distal end of the cannula set 10 is near the area directly above the suction port 12. The magnet 21 contained within this area of the suction capsule component 2 attracts the metal end of the cannula set 10 and holds it in the aligning grooves 14 of the capsule 2. The receiving cannula catch 70 is then actuated to releasably hold the initial delivery cannula set 1, which will now serve as a receiving cannula set 5.

The needles 16 that have passed through the initial receiving cannula set 5 are now flipped or turned around and reinserted, needle point first, into the proximal end of the initial receiving cannula set 5. Tension is held on the suture slack 4 as the needles 16 are advanced down the initial receiving cannula set 5 until the needles distal tips are aligned with the distal end of the initial receiving cannula set 10. This loaded cannula set now becomes the new delivery cannula set 1.

Figure 19D:
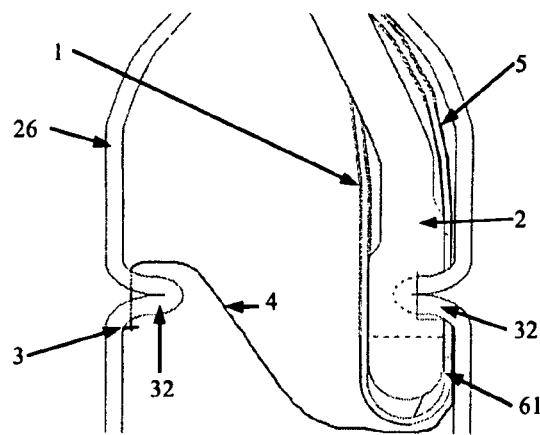
FIG. 19D illustrates a sectional view of the device components in use.

Referring to FIG. 19D, the new delivery cannula 1 is warped by actuating the warping cable 6. Suture slack 4 is managed by tension applied to the suture out of the proximal end of the new delivery cannula set 1 by the operator.

The new delivery cannula set 1 is coupled to the suction capsule component 2 and releasably held in place with the distal tips of the cannula set 10 positioned distal to the suction opening 12.

The device is now armed and ready to engage the next tissue. The attached or enclosed endoscope 15 moves the device so that the suction opening 12 is adjacent to the next tissue intended for suture incorporation.

The vacuum is again engaged and tissue is drawn into the bore of the suction capsule component 2.

The needles 16 are advanced through the drawn in tissue and continue up the receiving cannula set 5 until they emerge out of the receiving cannula set's 5 distal end. The needles 16 are grasped and pulled completely through.

The receiving cannula set 5 is released from the suction capsule component 2.

Figure 19E:
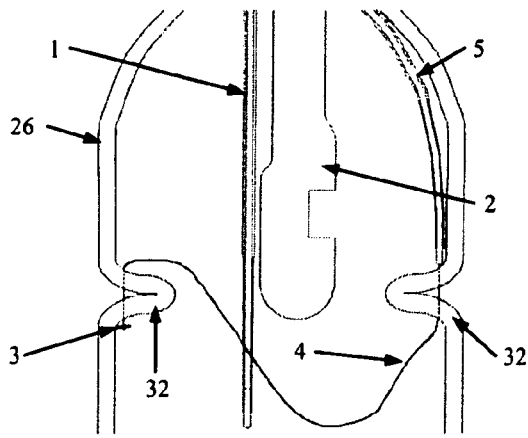
FIG. 19E illustrates a sectional view of the device components in use.

Referring to FIG. 19E, the recent delivery cannula set 5 is reconfigured into a straight configuration, disengaging from the suction capsule component 2.

The suction capsule component 2 is repositioned such that the recent delivery cannula set 1 is positioned adjacent to the front of the suction capsule component 2. The recent delivery cannula set 1 is coupled with the suction capsule component 2 as described earlier, now positioned to serve the function of a receiving cannula set 5.

Figure 19F:
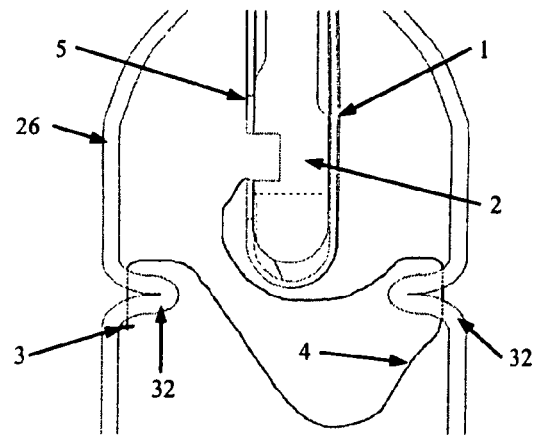
FIG. 19F illustrates a sectional view of the device components in use.

Referring to FIG. 19F, the needles 16 that have passed through the receiving cannula set 5 are now flipped around and reinserted into the proximal end of the recent receiving cannula set 5. Tension is held on the suture slack as the needles 16 are advanced until their distal tips are aligned with the distal end of the recent receiving cannula set 10. This loaded cannula set now becomes the new delivery cannula set 1.

The new delivery cannula set 1 is warped by actuating the warping cable 6. Suture slack 4 is managed by tension applied to the suture 4 by the operator. The new delivery cannula set 1 is coupled to the suction capsule component 2 and releasably held in place with the distal tips of the new delivery cannula set 10 positioned distal to the suction opening 12.

The suturing procedure can be performed again and again in the manner described above. The sutures can be tied or secured at anytime following a suture bite by drawing the sutures 4 taught, withdrawing the receiving cannula set 5, and endoscopically tying or securing the suture arms 4.

When suturing using a delivery cannula set with two or more cannulas, the ability of the cannula set to warp in multiple directions allows the operator to choose any location desired for a second tissue bite. If using a delivery cannula set that only warps in one direction, the operator needs to take care that a second tissue bite location was not selected that would necessitate the sutures to cross each other between bites.

Figure 28A:
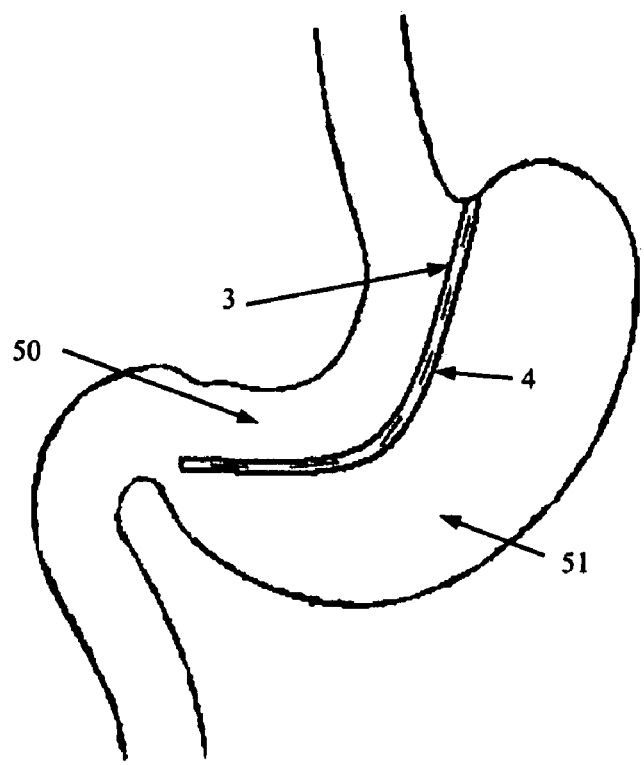
FIG. 28A illustrates a view of a stomach with incorporated linear grafts forming a tube or compartment within the stomach with limited volume.
Figure 28B:
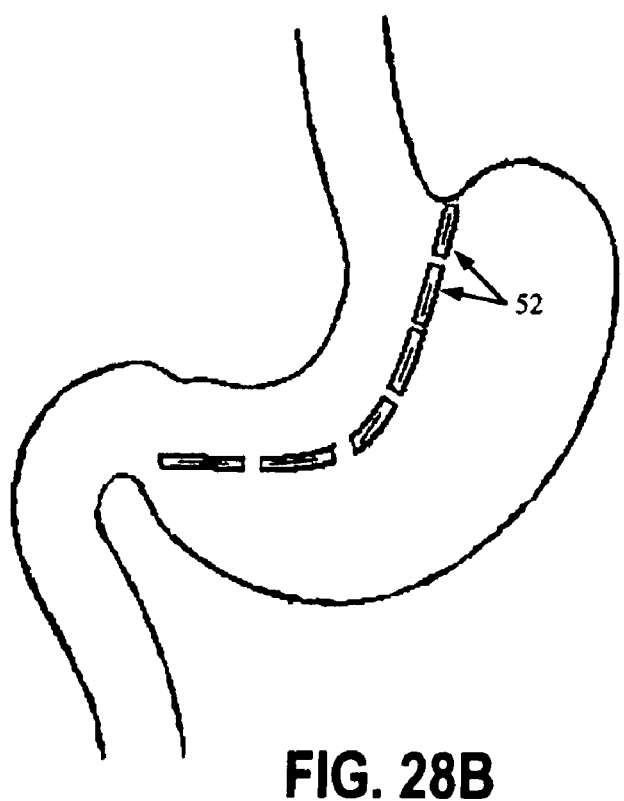
FIG. 28B illustrates a view of a stomach with incorporated line of pledgetted suture bites forming a tube or compartment within the stomach with limited volume.

Referring to FIGS. 28A and 28B, if the intent is to produce a series of interrupted mattress suture bites, a delivery cannula set 1 loaded with a new double-armed suture 16 & 4 may be inserted into the suturing site after each preceding set of suture bites. The individual mattress suture bites may include pledgets 52. The individual mattress suture bites may be tied or secured immediately after their deployment, or alternatively they may be tied after some or all of the required suture bites have been incorporated into tissue. The suture arms of the unsecured suture arms from proceeding suture bites may be maintained in receiving cannula sets 5 until the time comes to secure them.

Figure 20:
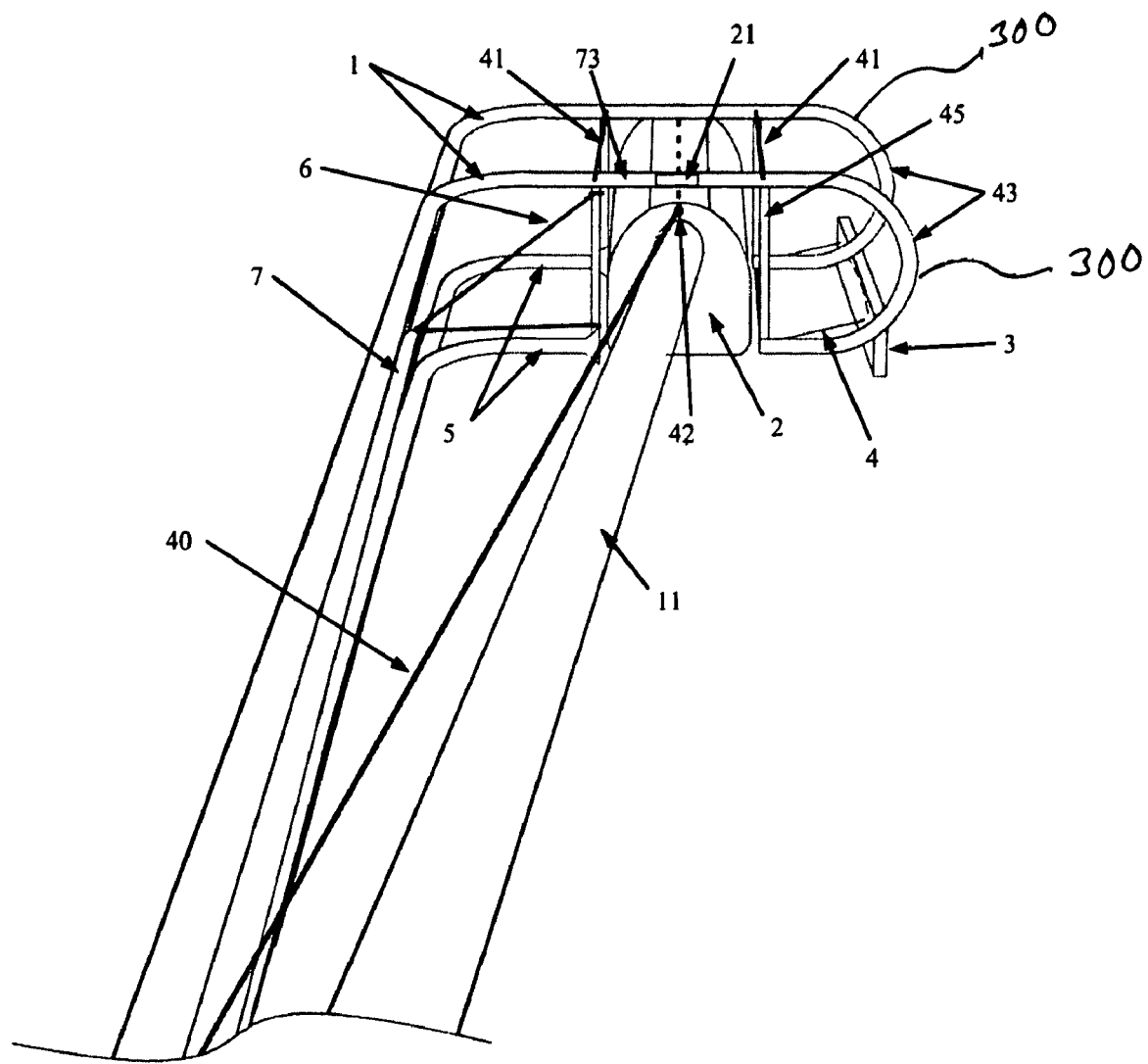
FIG. 20 illustrates a view of an embodiment of the invention for placing a suture within tissue in a perpendicular relation to the suction capsule component.

FIG. 20 illustrates two exemplary cannula units 300, and a linear suction capsule component 2 that couples substantially perpendicular with a portion of at least one pair of delivery and receiving cannulas 1 and 5 within cannula unit 300. Cannula unit 300 form sutures in tissue such that they cross suction port 12 perpendicularly to suction capsule components 2 length.

Figure 25:
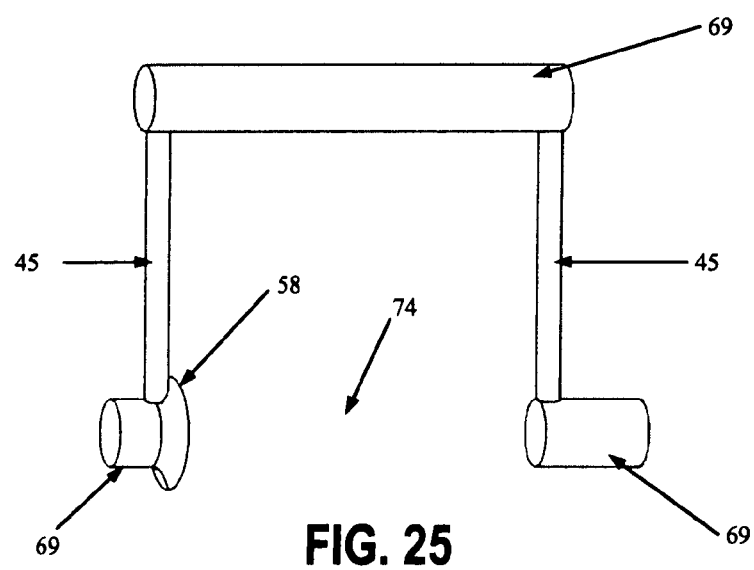
FIG. 25 illustrates a view of a rigid frame for holding delivery and receiving cannula around a suction capsule component.

In suturing device 100, the delivery cannula 1 is held with a fixed loop 43 near its distal end. Delivery cannula 1 may be supported and maintained in its looped configuration by a rigid frame 73 that spans the area of incorporation with the linear suction capsule component 2. Rigid frame 73, as illustrated in FIG. 25, may be made up of a rigid top lumen 69, rigid vertical support shafts 45 on opposing sides of the frame opening 74, and rigid cannula attachment lumens 69. The rigid cannula attachment lumens 69 on either side of frame opening 74 may be aligned to permit a needle to exit one cannula, cross the frame opening 74, and enter and continue within the second cannula. Rigid frame 73 may connect delivery cannula 1 and the receiving cannula 5 together as a unit.

The distal end of the cannula units 300 may be connected to one another by lengths of material acting as lengthwise cannula unit connectors 41. These connecters 41 may attach to the rigid frames 73 at their four corners. They may attach on or near the internal perimeter corners of the rigid frame 73, or they may attach on or near the external perimeter corners of the rigid frame 73, or any combination of internal corner and external corner connections. These lengthwise cannula unit connecters 41 may be made of a flexible material. Some materials may include, wire, thread, string, fabric, cable or other similar length of material.

Figure 21:
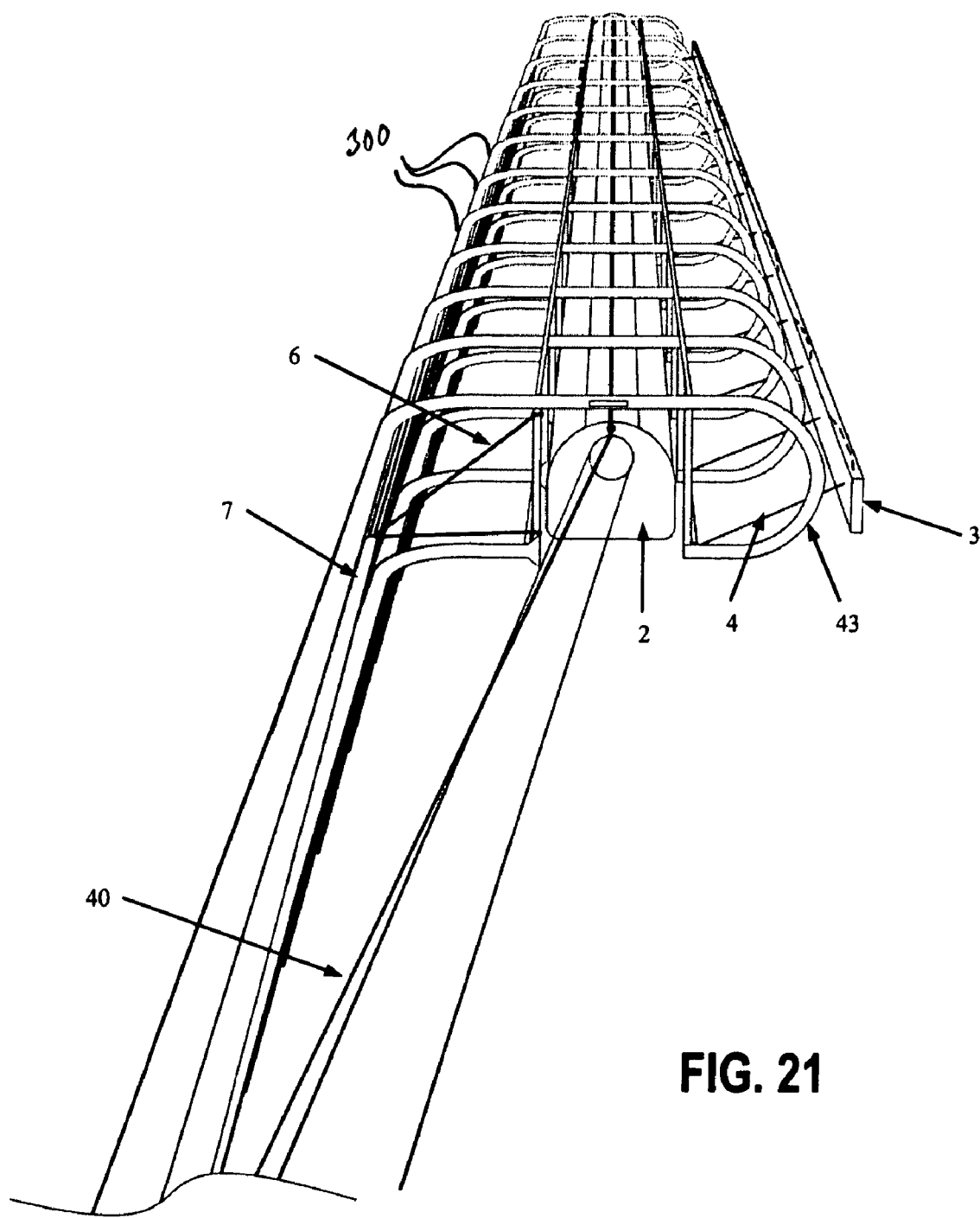
FIG. 21 illustrates a view of an embodiment of the invention for placing multiple sutures within tissue in a perpendicular relation to the suction capsule component.

Referring to FIGS. 20 and 21, the warping cable 6 may be attached to the most proximal frame 73 at one or more locations. Warping cable 6 may be actuated as described earlier by pulling cable 6 through warping cable lumen 7. This will pull frame 73 toward the distal end of warping cable lumen 7, creating an angle of approximately 90 degrees between the distal cannula segment distal to the distal end of the warping cable lumen 7 and the lengths of delivery and receiving cannula shafts proximal to the distal end of the warping cable lumen 7. The cannula units distal to the first or most proximal cannula unit are also warped in unison with the first or most proximal cannula unit by the action of the warping cable 6 because they are attached to the first by the lengthwise cannula unit connecters 41.

A device 100 having cannula units 300 may be inserted into a suturing site in a non-warped or relatively straight configuration. Linear suction capsule component 2 may be inserted into the suturing site subsequent to the insertion of suturing device 100. Linear suction capsule component 2 may be guided into its intended position of incorporation with the cannula sets by the use of a guide wire 40, which is attached to the center of the rigid top lumen 69 of the most distal rigid frame 73. Linear suction capsule component 2 may have a lumen or channel 42 through which the guide wire 40 can pass. The most proximal rigid frame in the cannula unit 300 may have a magnet 21 or be able to be attracted by a magnet 21 that may be contained by the linear suction capsule component in the side opposite to the suction opening 12 on the proximal portion of the linear suction capsule component 2, as illustrated in FIGS. 20-23D.

FIG. 21 illustrates a device with 12 cannula units 300 connected together in its warped configuration with suction capsule component incorporated 2. The double-armed suture needles are back-loaded into the delivery cannulas 1, with a linear graft 3 incorporated into the suture loops 4.

Figure 22A:
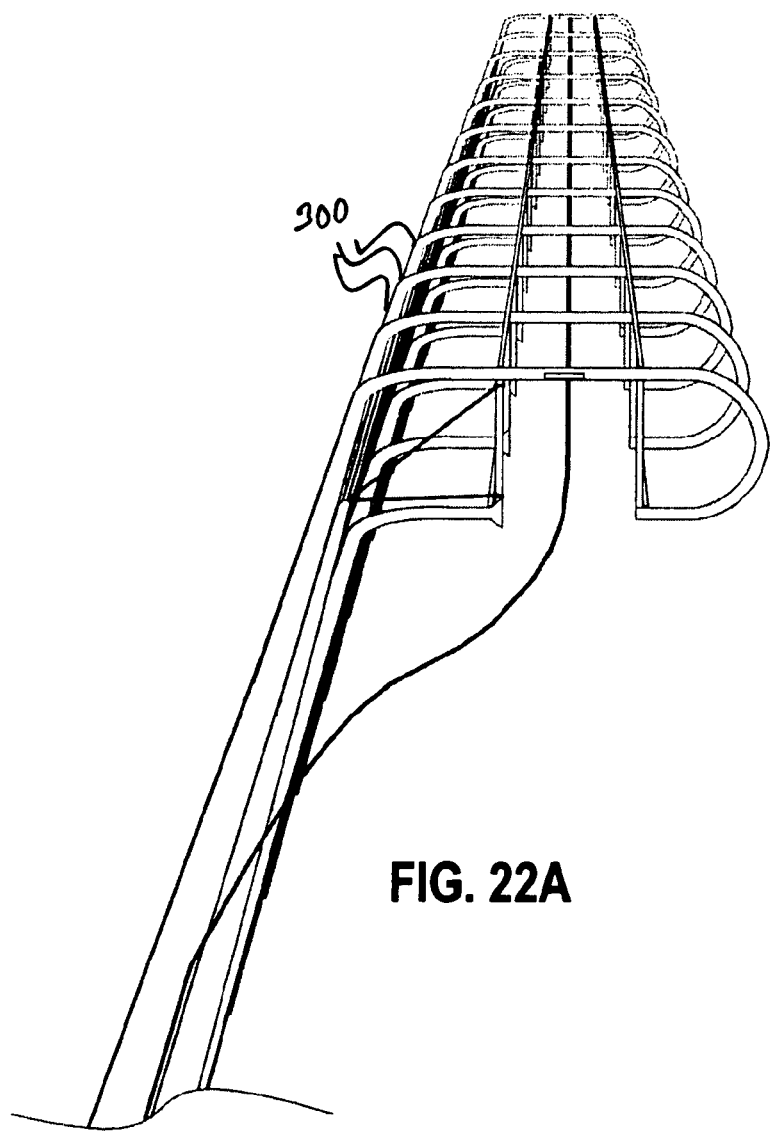
FIG. 22A illustrates a view of multiple delivery and receiving cannulas without the linear suction capsule component incorporated.
Figure 22B:
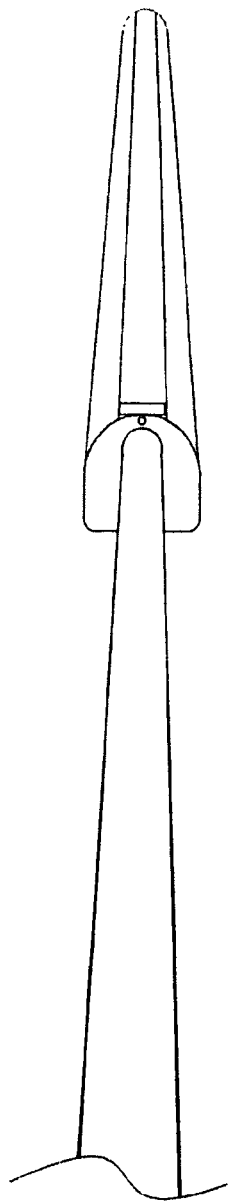
FIG. 22B illustrates a view of a linear suction capsule component.

FIGS. 22A & 22B respectively illustrate a cannula unit component and a linear suction capsule component 2 independent of each other.

FIG. 23A illustrates a view of the top or side opposite to the suction opening 12 of a linear suction capsule component 2. The tubular structure 11 connecting the linear suction capsule component 2 to a vacuum source may run within an endoscope's 15 working channel, or it may run along side of an endoscope 15, or alternatively it may contain an endoscope 15. Tubular structure 11 may be attached to the distal end of an endoscope 15, or alternatively exist independent of an endoscope 15. The linear suction capsule component 2 may vary in length depending upon the number of cannula units 200 utilized. The length generally spans at least the distance from the rigid top lumen 69 of the most proximal cannula unit to the rigid top lumen 69 of the most distal cannula unit. The linear suction capsule component 2 may extend beyond these points. Lengths may vary from about 10 mm to about 200 mm. The cross section of the linear suction capsule component 2 may be circular, semi-circular, oval, rectangular, or irregular. The diameter or combination of height and width may be of a size that is amenable to insertion through a natural body orifice. The diameter of the linear suction capsule component may vary from approximately 5 mm to 20 mm. The length and width of the linear suction capsule component may be able to expand and contract within a hollow organ or body cavity after insertion. The length may be varied by a telescoping feature. The diameter may be varied by a collapsing or folding feature. The linear suction capsule component may be made of many materials, such as plastic or metal. The linear suction capsule component may be made of a material that is transparent, translucent, or opaque.

FIG. 23B illustrates a view of the bottom or side of the linear suction capsule component 2 with the suction opening 12. The suction opening 12 may run the approximate length of the linear suction capsule component 2 and may span the approximate width of the linear suction capsule component 2. The depth of the cavity of the suction port or opening 12 may be the approximate height of the linear suction capsule component 2, less a screened off portion at the top of the cavity 12. The top of the interior of the linear suction capsule component 2 may be partitioned off by a screen 47. This screened off compartment created at the top of the suction port cavity 12 allows the vacuum delivered to the capsule by the tube 11 to be in communication with the entire length of the linear suction capsule 2. Without this screened off compartment, tissue drawn into the capsule 2 that contacted the entire cross sectional perimeter of the interior surface of the capsules cavity 12 may block the vacuum's effect to and tissue distal to the blockage.

FIGS. 23C & 23D illustrate a view of an articulating linear suction capsule component 2. The suction capsule component may be made up of segments 48 that are attached to one another but that allow lateral and vertical bending of the suction capsule component 2 at the segment's points of attachment 49. This may allow for placement of a curved suture line or graft placement. This may also facilitate insertion of the component through a natural body orifice.

Figure 24:
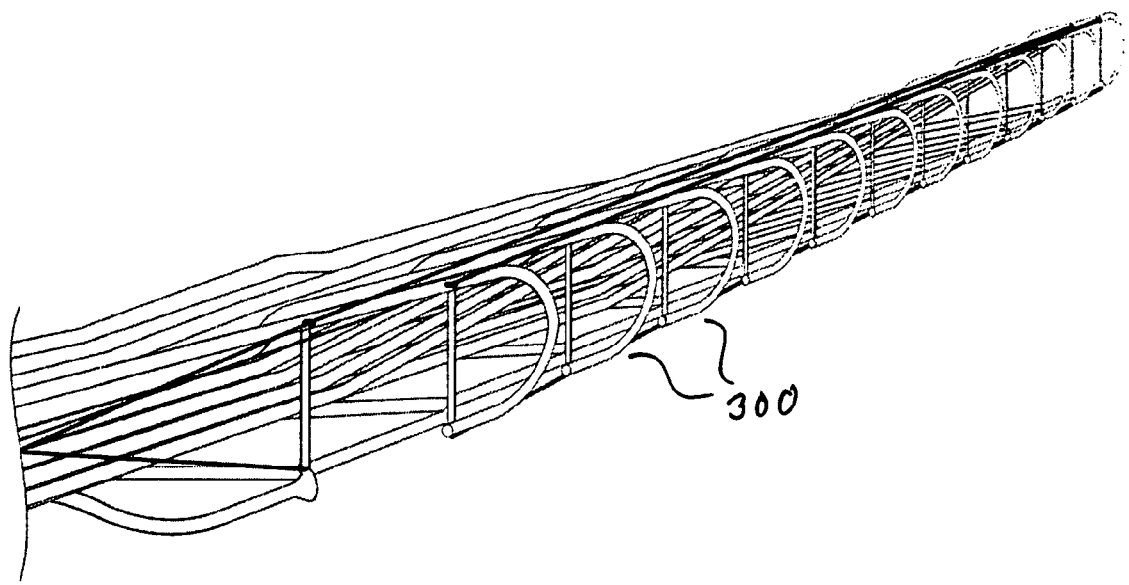
FIG. 24 illustrates a view of an embodiment of the invention for placing multiple sutures within tissue in a perpendicular relation to the suction capsule component in a folded configuration.

To facilitate the insertion of the series of cannula units 200, the device may be delivered or inserted into the suturing site in a collapsed configuration as illustrated in FIG. 24. There may be no or limited tension of the warping cable in this configuration and the looped ends of the delivery cannulas 43 provides an atraumatic leading edge for insertion. The device may also be in this configuration when the device is withdrawn from the patient.

In many instances it is important to use mattress sutures when connecting tissue, reconfiguring tissue, and or attaching grafts to tissue. Use of pledgets or bolstering material is also important for providing durability to a fix and or repair and or augmentation and or graft implantation provided by the sutured tissue. Mattress suture bites may be produced by using a double-armed suture. Pledgetted mattress suture bites may be produced by incorporating a pledget on the loop of suture between the two needles of a double-armed suture. The device allows the delivery of pledgetted and non-pledgetted double-armed sutures.

Figure 26A:
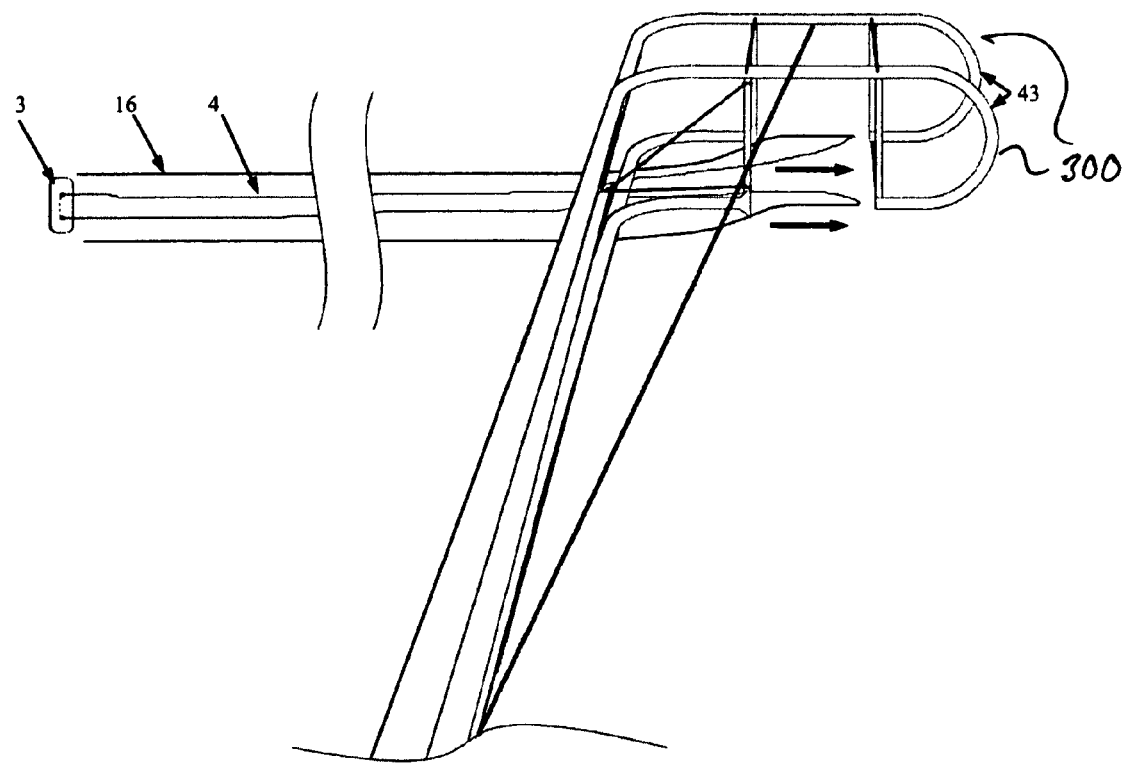
FIG. 26A illustrates a view of how a double-armed suture with an graft incorporated is back-loaded into a set of delivery cannulas.
Figure 26B:
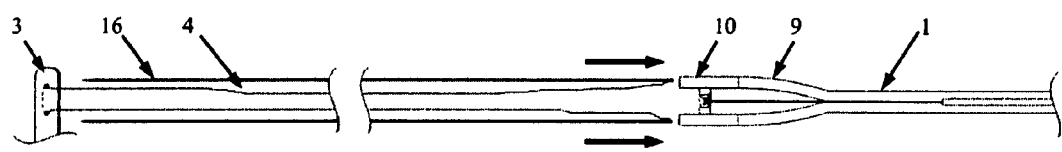
FIG. 26B illustrates a view of how a double-armed suture with an graft incorporated is back-loaded into a delivery cannula set.

FIGS. 26A & 26B illustrate how a double armed suture may be back-loaded into a set of delivery cannula lumens 1. The needles 16 are backed into the lumens with their attached suture 4 riding next to it within the lumen until the point of the needle 16 is within the distal end 10 of the delivery cannula.

In this embodiment, when in use, the cannula unit 300 would be inserted into a suturing site such as a hollow organ or body cavity. The distal end of the cannula unit 300 may be warped to its expanded configuration. The linear suction capsule component 2 with the optionally incorporated endoscope 15 may be slid down the guide wire 40 into its position of incorporation with the cannula unit. The suction opening 12 of the linear suction capsule component 2 may be positioned adjacent to the tissue intended of suture incorporation and the vacuum is activated. Tissue is drawn into the suction opening 12, which occupies the cavity of the linear suction capsule component 2. The at least one needle 16 may now be advanced through the at least one delivery cannula 1, thereby crossing the open side 74 of the rigid frame 73, thereby penetrating and traversing the tissue held in place between the at least one delivery cannula 1 and the at least one receiving cannula 5. The at least one needle 16 enters and continues on within the lumen of the at least one receiving cannula 5 until the at least one needle 16 exits the at least one receiving cannula's proximal end. The at least one needle 16 may then be grasped and pulled completely through until the loop of suture, which may include an incorporated pledget or graft 3, reaches the incorporated tissue.

The vacuum may be deactivated and the linear suction capsule component 2 may be withdrawn from the suturing site. The cannula units 300 may be straightened and withdrawn from the suturing site. The suture arms 4 of the incorporated suture loop or loops will trail out of the receiving cannula or cannulas 5 as the cannula unit is withdrawn.

There are several possibilities of what can be done next. The sutures 4 can be tied or secured. Or, a second graft 35 can be incorporated with the sutures 4, inserted into the suturing site with a graft pusher 29 and then tie or secure the sutures 4. Or, the device may be reloaded by fully withdrawing the needles 16 and sutures 4 from the distal end or the receiving cannulas 5 and then backing the needle 16 and attached suture 4 into its corresponding delivery cannula 1 as illustrated in FIG. 26A. The cannula unit 300 may then be reinserted into the suturing site with the operator managing the suture slack between cannula unit 300 and the point of suture incorporation with tissue by maintaining tension on the suture strands as they exit the proximal end of the delivery cannulas 1. With cannula unit 300 reloaded an reinserted within the suturing site, cannula unit 300 may be warped or reconfigured into its expanded configuration. The linear suction capsule component 2 may now be reinserted and incorporated with cannula unit 300. The suturing device 100 device may now be positioned adjacent to a second tissue intended for suture incorporation. The suturing procedure may be duplicated as described earlier. Suturing device 100 may be reloaded and engaged again and again, or the sutures 4 may be secured with or without a second graft 35.

Figure 27A:
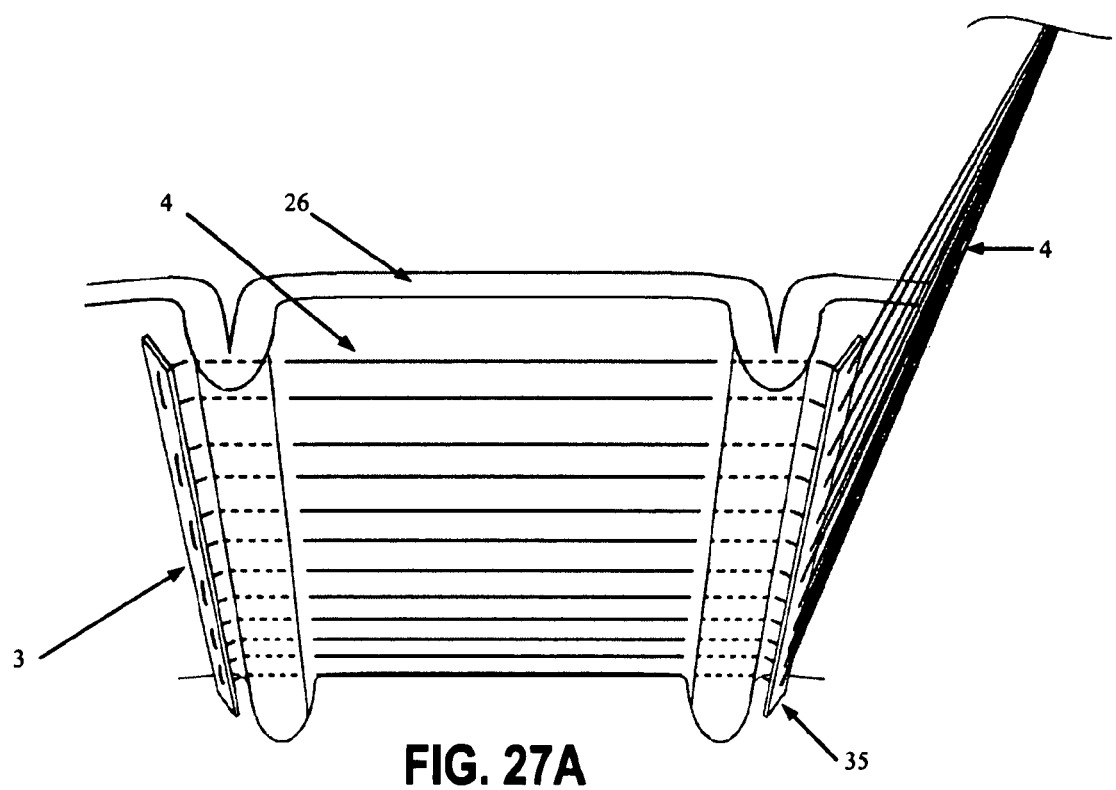
FIG. 27A illustrates unsecured linear grafts and sutures incorporated into tissue folds.
Figure 27B:
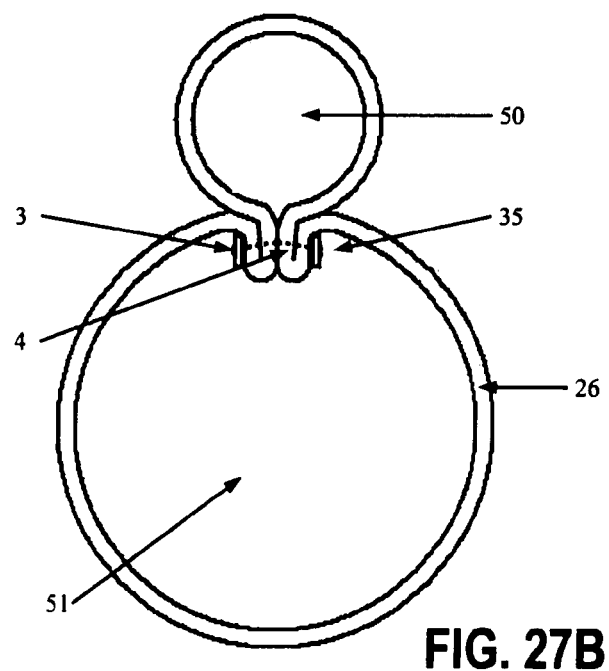
FIG. 27B illustrates secured linear grafts and sutures incorporated into tissue folds.

FIG. 27A illustrates two linear folds of tissue with sutures 4 and grafts incorporated 3 and 35. Sutures 4 may be endoscopically pulled taught and tied or secured. The result may be two smaller lumens 50, 51 created from within one larger lumen as illustrated in FIG. 27B by the cross sectional view of a stomach with grafts and sutures secured. FIG. 28A illustrates an internal view of secured linear grafts 3 and 35 within the stomach, and FIG. 28B illustrates a line of individual pledgetted mattress sutures 52 within the stomach.

The result of the reconfigured stomach may create a narrow lumen 50 meant to limit the amount of food a patient can intake. The other lumen or residual stomach pouch 51 may be intact and may be in communication with the small bowel, allowing the flow of digestive fluids to escape the pouch 51.

In another embodiment, suturing device 100 may be configured so that it is suited for closing incisions or defects within a hollow organ or body cavity. FIGS. 29A-31 illustrate front and side views of an embodiment of the device configured to close incisions or defects.

FIGS. 29A-31 illustrate a suturing device 400 in which there are six delivery cannula 1 lumens making up three pairs of delivery cannulas 1. There are also six receiving cannula 5 lumens making up three pairs of receiving cannulas 5. The delivery cannulas 1 run parallel to each other and may be contained within a tubular housing 59. The cross section of this housing 59 may be generally rectangular, with the delivery cannulas 1 arranged in two rows of three within. The distal ends of the delivery cannulas 1 may be free and not housed within the delivery cannula housing 59. The six receiving cannula 5 may be arranged in parallel with the delivery cannula housing 59 such that three receiving cannula 5 are positioned on opposite sides of the delivery cannula housing 59. The receiving cannulas 5 may be contained within a tubular housing 60. The distal ends of the receiving cannulas 5 may be free and not housed within the receiving cannula housing 60. The delivery cannula housing 59 may also contain two lumens 7 for containing the two warping cables 6.

FIG. 29A illustrates a front view of the suturing device 400 in its unexpanded configuration. Suturing device 400 may have the six delivery cannula distal ends configured into two series of three connected cannula distal ends. The delivery cannula 1 distal ends may be manipulated and reconfigured by increasing the distance between each cannula's 1 distal end of a connected series. This may be done by having a connecting bar 54 attached to all three distal cannula tips 1 at the same distance from their distal ends. Pushing or pulling up on the delivery cannula 79 on the side opposite to the delivery cannula 75 fixed in the delivery cannula housing 59, may expand or retract the spread of the three delivery cannula tips 1, as illustrated in FIGS. 29B & 30B. The connecting bar 54 may attach two or more cannulas 1 creating a connected series of cannula tips.

The distal ends of the delivery cannulas 1 may also be reconfigured so that their distal ends form a loop 61. This may be accomplished by actuating or pulling the warping cable 6 that may be attached to the connecting bar 54. The warping cable 6 may have a spacer 55 incorporated around the cable that allows a stable and designed distance between the connector bar 54 and the housing of the delivery cannula 59 when the cannulas 1 are in a warped configuration, as illustrated in FIGS. 29C and 30C. The warping cable 6 may be attached to the midpoint of the connecting bar 54.

Figure 31:
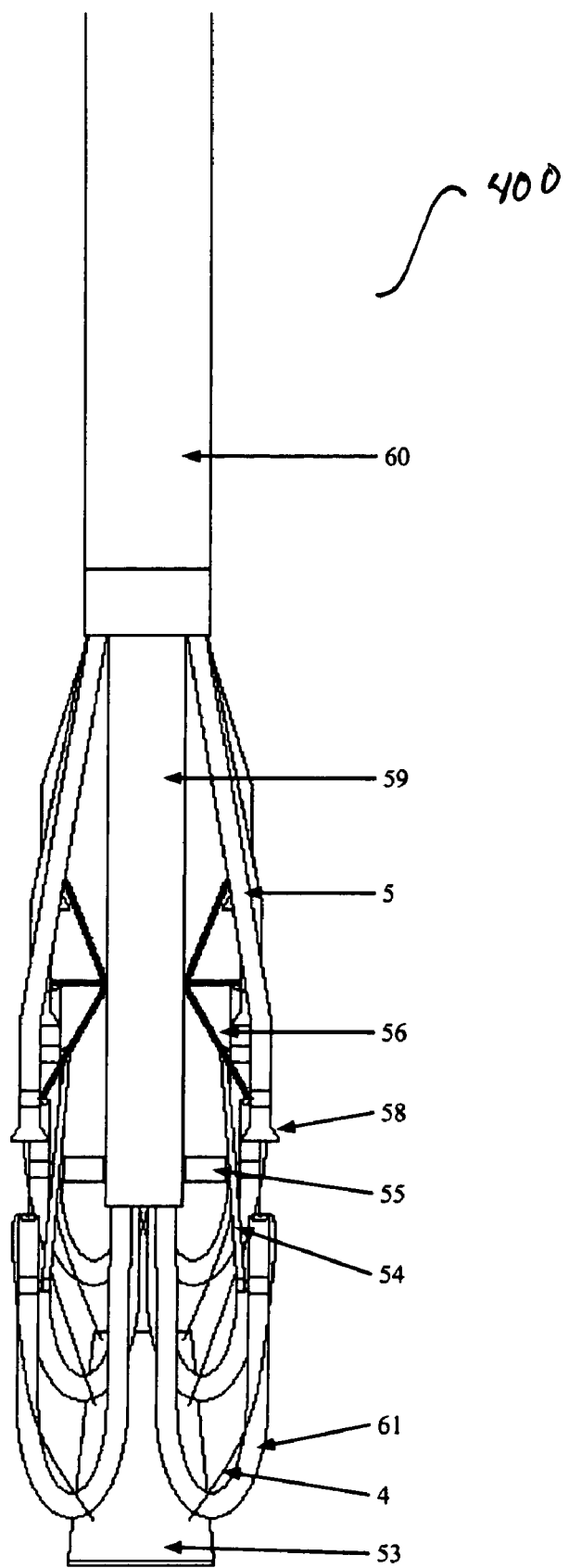
FIG. 31 illustrates a side view of an embodiment of the invention that delivers sutures within a hollow organ to close an incision or defect with the delivery cannula tips spread and warped upwards and the receiving cannula tips extended.

The housing 60 containing the receiving cannulas 5 may be able to slide longitudinally over the housing 59 containing the delivery cannulas 1. As illustrated in FIGS. 29D, 30D, and 31, the distal ends of the receiving cannulas 5 are attached to struts 56 that are attached to the housing of the delivery cannula 59. When the receiving cannula housing 60 containing the attached receiving cannulas 5 is actuated and advanced down the delivery cannula housing 59, the distal tips of the receiving cannula 5 may be expanded outward, similar to the expansion of an umbrella.

As illustrated in FIGS. 30C, 30D, & 31, double-armed sutures may be back-loaded as described earlier into cannula pairs such that one needle is backed into one cannula 1 in one connected series of cannulas, and the second needle is backed into a cannula opposite to the first in the second connected series of cannulas. This will produce a span of suture 4 between the two cannula tips.

The span or loop of suture 4 formed at or near the middle of the length of suture of the double-armed suture may incorporate a graft or patch 53. This patch 53 may be releasably held or maintained between the two series of delivery cannula distal ends 1 during insertion prior to the devices warping, as illustrated in FIGS. 29A, 29B, 30A, & 30B. When the distal ends of the delivery cannulas 1 are warped, the graft may descend to a position beneath of near the loops of the distal cannula 61 held in suspension by its incorporated suture spans 4, as illustrated in FIGS. 29C, 29D, 30C, 30D, & 31.

In use, as illustrated in FIG. 32A, device 300 may be contained within a thin plastic sheath 62 or condom. The sheath 62 may function to facilitate insertion of device 300 by covering and smoothing the multiple surfaces of the distal delivery and receiving cannulas 1, 5. The sheath 62 may also function to keep device 300 sterile through the insertion process and until delivery of device 400 through the incision or defect 63 intended for suture closure. As the internal lumen of the digestive system contains may contaminates, keeping device 400 sterile prior to introducing it through a break or defect 63 in the digestive system's wall may be important. Device 400 may easily penetrate through the sheath's 62 distal end prior to deployment through the incision or defect 63.

FIGS. 32B-32F demonstrate insertion of device 400 through an incision or defect 63, reconfiguration or expansion of device 400, deployment of the sutures 4 with incorporated patch 53, collapsing of device 400 and withdrawing of device 400, and a secured set of sutures 4 holding a patch 53 in place distal to the closed incision or defect 53. In this embodiment, device 400 may work in concert with an endoscope 15 placing the distal end of device 400 in or near the incision or defect 63. Alternatively, device 400 may be connected to an endoscope 15 so that it may move directly by the movement of the endoscope 15. FIG. 32B illustrates the distal ends of the delivery cannulas 1 passed into and through the incision or defect 63. The delivery cannula series 1 are actuated such that their distal ends spread as the connecting bar 54 is brought perpendicular with the three delivery cannula tips 1.

Figures 32C, 32D:
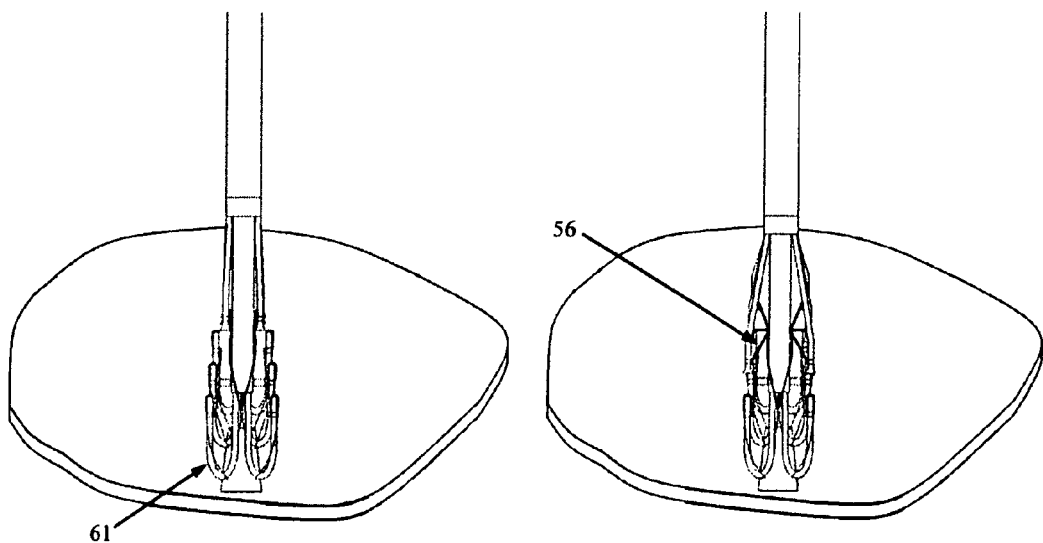
FIG. 32C illustrates a view of an embodiment of the invention with delivery cannula tips passed through the incision or defect and with the delivery cannula tips spread and warped upwards.
FIG. 32D illustrates a view of an embodiment of the invention with delivery cannula tips passed through an incision or defect and with the delivery cannula tips spread and warped upwards and the receiving cannula tips extended.

With the distal ends of the delivery cannulas 1 positioned on the distal side of the incision or defect 63, the warping cables 6 may be actuated such that they reconfigure the distal end of the delivery cannulas creating a loop 61, as illustrated in FIG. 32C, wherein the distal ends of the delivery cannulas 1 are distal to the tissue wall 26 containing the incision or defect 63 and are directed at the tissue wall 26.

The distal ends of the receiving cannulas 5, positioned on the proximal side of the tissue wall 26 with the incision or defect 63 may by actuated by sliding the receiving housing unit down 60, thereby extending the struts 56 attached to the distal ends of the receiving cannulas 5. The distal ends of the receiving cannulas 5 may still be proximal to the tissue wall 26 containing the incision or defect 63 and are directed at the tissue wall 26. The distal ends of the receiving cannulas 5 may also be configured such that they are directly aligned with the looped distal ends of the delivery cannulas 1, as illustrated in FIG. 32D.

Long flexible needles 16 with attached sutures 4 are advanced through the delivery cannulas 1 and pass through the tissue 26, which is positioned between the distal ends of the delivery and receiving cannulas 1 and 5. Needles 16 enter the receiving cannulas 5 and continue up until the tips of needles 16 emerge out of the proximal ends of the receiving cannulas 5. The tips of needles 16 may be grasped and pulled completely through the receiving cannulas 5 until the full length of the suture arms 4 have been drawn through.

Figures 32E, 32F:
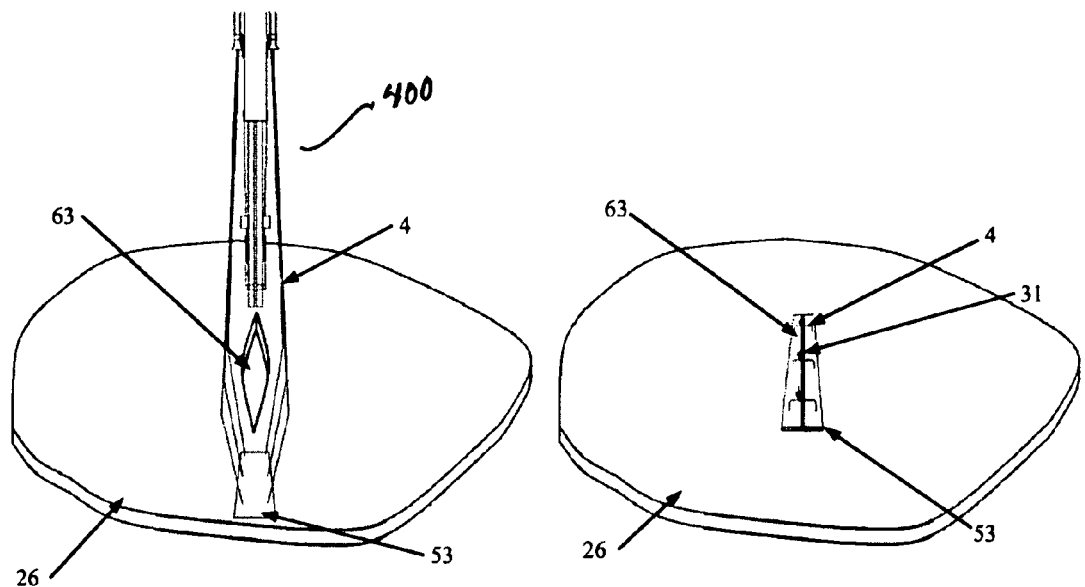
FIG. 32E illustrates a view of an embodiment of the invention with sutures deployed through and out of the delivery cannulas and passing through the tissue and up into the receiving cannulas.
FIG. 32F illustrates a view of a patch secured by sutures on the distal side of an incision of defect in a tissue wall.

Device 400 may now be returned to its original configuration and withdrawn from the incision or defect 63 and from the patient. The suture arms 4 may trail out of the distal ends of the receiving cannula 5 as the device is pulled from the suture site, as illustrated in FIG. 32E. A second or proximal patch (not shown) may be incorporated with the sutures 4 if desired. The sutures 4 may be tied or secured endoscopically, as illustrated in FIG. 32F. The patch 53 may be made of or coated by an antibacterial agent, bioadhesive, anti-inflammatory, hemostatic agent, or any combination there of.

Figures 33A, 33B, 33C:
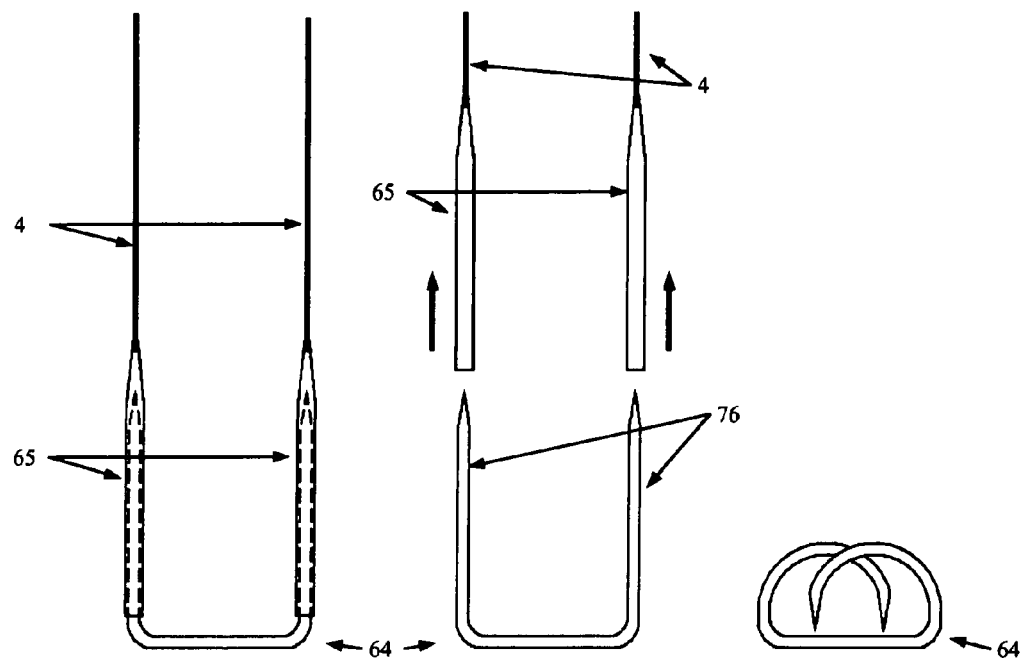
FIG. 33A illustrates a view of an exemplary clip with shape memory with its tangs held in a straight configuration by rigid tubes attached to sutures.
FIG. 33B illustrates a view of a clip with shape memory with the rigid tubes attached to sutures pulled off the tangs.
FIG. 33C illustrates a view of a clip with shape memory configured to its shape-set configuration.

FIGS. 33A-33C illustrate a shape memory self-fixing clip 64 that may be utilized by device 300 for securing tissue. Clip 64 may be made of a material that possesses shape memory, such as Nitinol. The tangs 76 of clip 64 may be shape set such that they naturally have a bend or curl in their lengths as illustrated in FIG. 33C. Tangs 76 may be temporarily held in an other configuration, such as straight. Tangs 76 may be held in a straight configuration by being confined and contained within a tube 65, which may be straight and rigid. Tube 65 may be releasably held by the tang 76 by the tension that the tang 76 applies to the internal lumen of the tube 65 created by the tang's 76 tendency to want to return to its shape set or curved configuration, as illustrated in FIG. 33A. Tubes 65 may have a tapered point and be attached to a length of material such as a suture 4. When the sutures 4 pull their attached tubes 65 with enough force to release the tang's 76 hold on them, the tubes 65 release the clip's tangs 76, enabling the clip 64 to return to its shape set configuration.

Figure 34A:
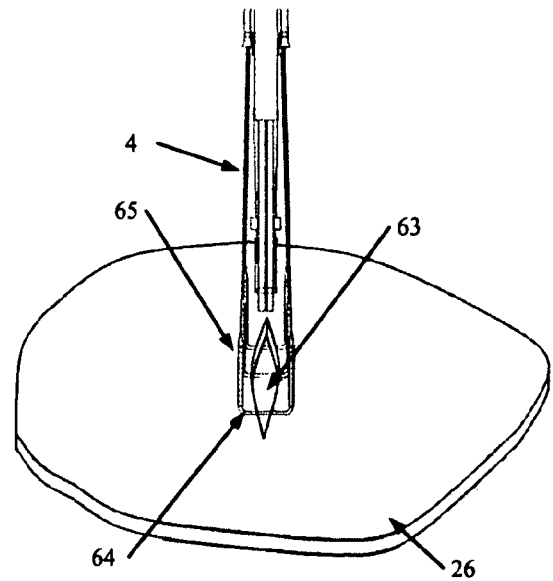
FIG. 34A illustrates a view of an embodiment of the invention deploying clips with shape memory.
Figure 34B:
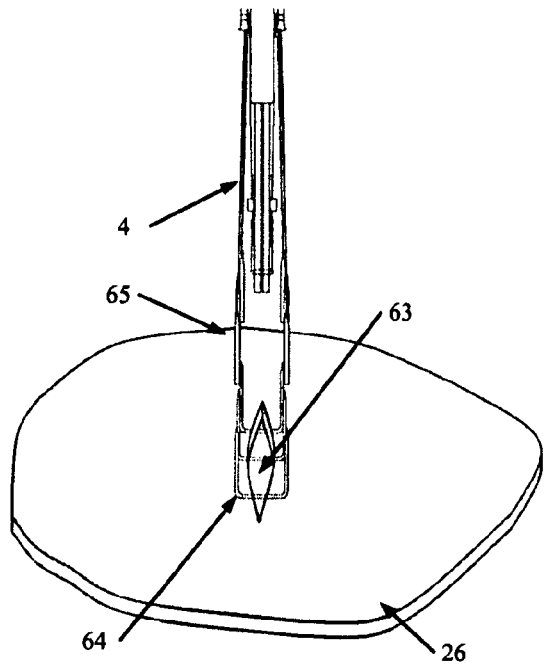
FIG. 34B illustrates a view of an embodiment of the invention further deploying clips with shape memory.
Figure 34C:
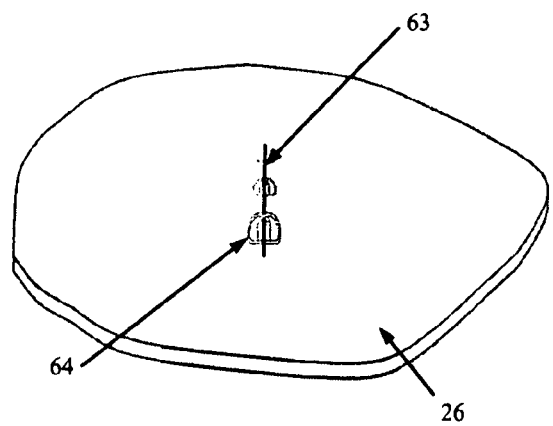
FIG. 34C illustrates a view of clips with shape memory deployed and closing an incision or defect.

FIGS. 34A-34C illustrate a shape memory self-fixing clip 64 that may be utilized by a device configured to close an internal incision or defect 63. The shape memory self-fixing clips 64 may be incorporated with long flexible needles 16 and suture 4 such that the clip is held between of two lengths of suture, with each length of suture 4 attached to a needle 16 at one end and to a tube 65 for releasably holding a clip tang 76 at the other end. The shape memory self-fixing clips 64 may be held by the device similar to the patch 53 described earlier, or they may hang freely distal to the distal ends of the delivery cannulas 1. The needles 16 may be incorporated with tissue as described earlier, incorporating the tubes 65 releasably holding the shape memory self-fixing clip 64, as illustrated in FIG. 34A. Once the distal end of the device emerges on the proximal side of the incision or defect 63, tension may be applied to the suture arms 4 to pull the tubes 65 off of the tangs 76. Released from the confines of the lumen of tube 65, the tangs 76 immediately return to their shape set configuration, thereby clasping and fixing the tissue 26 held therein, as illustrated in FIG. 34C.

Figures 35A, 35B, 35C:
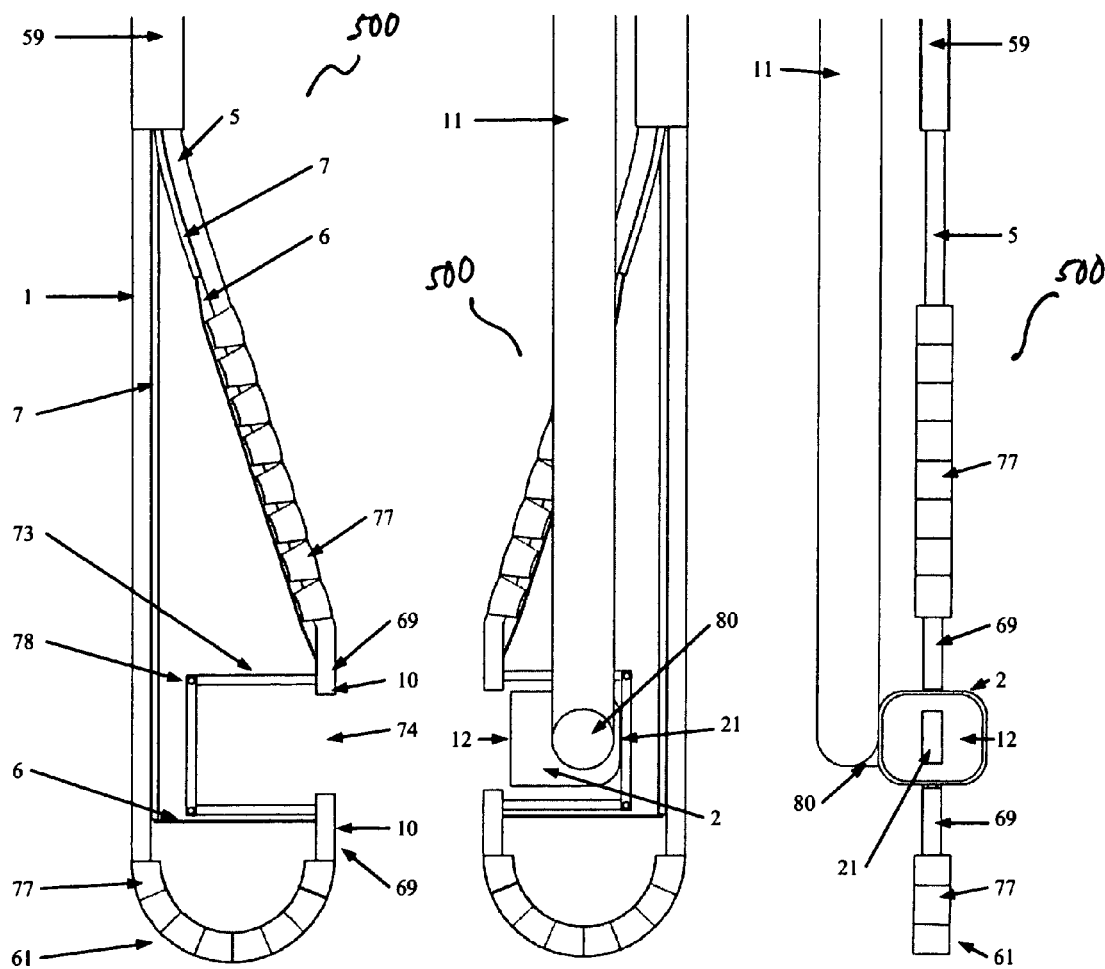
FIG. 35A illustrates a side view of another embodiment of the current invention configured to deliver a suture needle through its left cannula.
FIG. 35B illustrates a view of the embodiment of 35A configured to deliver a suture needle through its right cannula with a suction capsule component incorporated.
FIG. 35C illustrates a front view of the embodiment of 35A with a suction capsule component incorporated.

FIGS. 35A-35C illustrate a view of a suturing device 500 that enables continuous sewing or suturing within a hollow organ or body cavity. Device 400 has 2 flexible cannulas which may be held a constant distance apart by an inward curving or inward protruding rigid frame 73. In one embodiment, the frame 73 may be collapsible, folding at its hinge points 78. The length of the cannulas 1 and 5 may run up a common tube 59, and each may be contained such that each cannula length is able to slide up and down within the common tube 59. Each cannula 1 and 5 may be connected to or formed in parallel with a second lumen 7 designed to contain a warping cable 6. Warping cable 6 contained within the warping cable lumen 7 of each cannula 1 and 5 may be attached to the distal end of each cannula 1. The section of cannula 1 near the distal end that forms a loop 61 when warped contains or is formed with semi-circle shape defining wedges 77 on the exterior of the cannula. The wedges 77 enable the loop 61 to form a consistent shape and size loop 61 when the warping cable 6 is engaged. The wedges 77 allow cannula 1 to return to a straight configuration when the distal cannula 1 is not engaged by the warping cable 6. Rigid frame 73 is connected to or formed as a unit with the segment of rigid tubes 69 at the distal end of each cannula 1 and 5. These rigid tube segments 69 connected or formed with the rigid frame 73 are aligned such that a needle 16 may be passed from one cannula to the second, traversing the opening in the frame 74. By sliding the two cannulas 1 and 5 conversely in relation to each other within the common tube 59 and by actuating the two warping cables 6 conversely in relation to each other, device 400 is able to alternately configure each cannula's 1 and 5 position beneath or above the other.

A suction capsule component 2 may be incorporated with device 500 as illustrated in FIGS. 35B & 35C. The suction capsule component 2 may be attached to a tube 11 such that it may pivot on a joint 80. This joint 80 has a lumen that maintains a fluid communication between the tube 11 and suction capsule component 2 at each available angle of adjustment. The suction capsule 2 may be able to rotate to angles of ninety degrees in relation to opposing sides of the attached tube 11. The suction capsule component 2 may have a magnet 21 contained on the back side of the suction opening 12. This magnet 21 may releasably hold the suction capsule component 2 within the rigid frame 73 of the cannula unit. A groove 14 on the side opposite of the suction opening 12 of the suction capsule component 2 further allows proper alignment of the two components.

In use, device 500 and suction capsule component 2 may be inserted into the suturing site individually or coupled as a unit. If the components are inserted individually, they may be coupled once inside the hollow organ or body cavity intended for suturing. Alternatively, the suction capsule component 2 may first engage a targeted tissue by activating the vacuum, then subsequently be coupled with device 500. With device 500 coupled to the suction capsule component 2 and tissue drawn into the suction opening 12 of the suction capsule component 2, the needle 16 positioned in the looped or bottom cannula 1 may be advanced through the drawn in tissue. Once the tip of needle 16 emerges out of the proximal end of the receiving cannula 5, it may be grasped and pulled through. The vacuum may be deactivated and the tissue bite released. The tissue is now incorporated with a suture 4 running through it, continuing up into and out of the receiving cannula 5.

Needle 16 may now be turned around and reinserted into the proximal end of the receiving cannula 5 and advanced down until the needle tip is aligned within the distal end 10 of the receiving cannula 5. Needle 16 may have measuring markings on its shaft to indicate length increments. Device 500 may now be reconfigured by pulling the bottom cannula 1 within the common tube 59 so that the length of cannula exposed distal to the common tube 59 is shortened. Receiving cannula 5, now containing needle 16 and suture 4, is pushed within the common tube 59 so that the length of cannula exposed distal to the common tube 59 is lengthened. The warping cable 6 of the former bottom or empty cannula 1 may be disengaged, and the warping cable of receiving cannula 5, now containing suture 4 and needle 16 is engaged. The function of the two cannulas have been reversed and receiving cannula 5, which had been empty and serving to receive a needle 16, now contains a needle 16 and is configured to deliver needle 16. Further, delivery cannula 1, which had contained needle 16 suture 4 and had been serving to deliver needle 16 is now empty and is configured to receive needle 16, as illustrated in FIGS. 35A & 35B. Repeating this process allows an operator to suture continually within a closed space such as a hollow organ or body cavity.

The embodiment of the device described above may also function with multiple cannulas running parallel and positioned such that their distal ends are aligned with opposing cannulas on opposite sides of a rigid frame 73.

Figure 36:
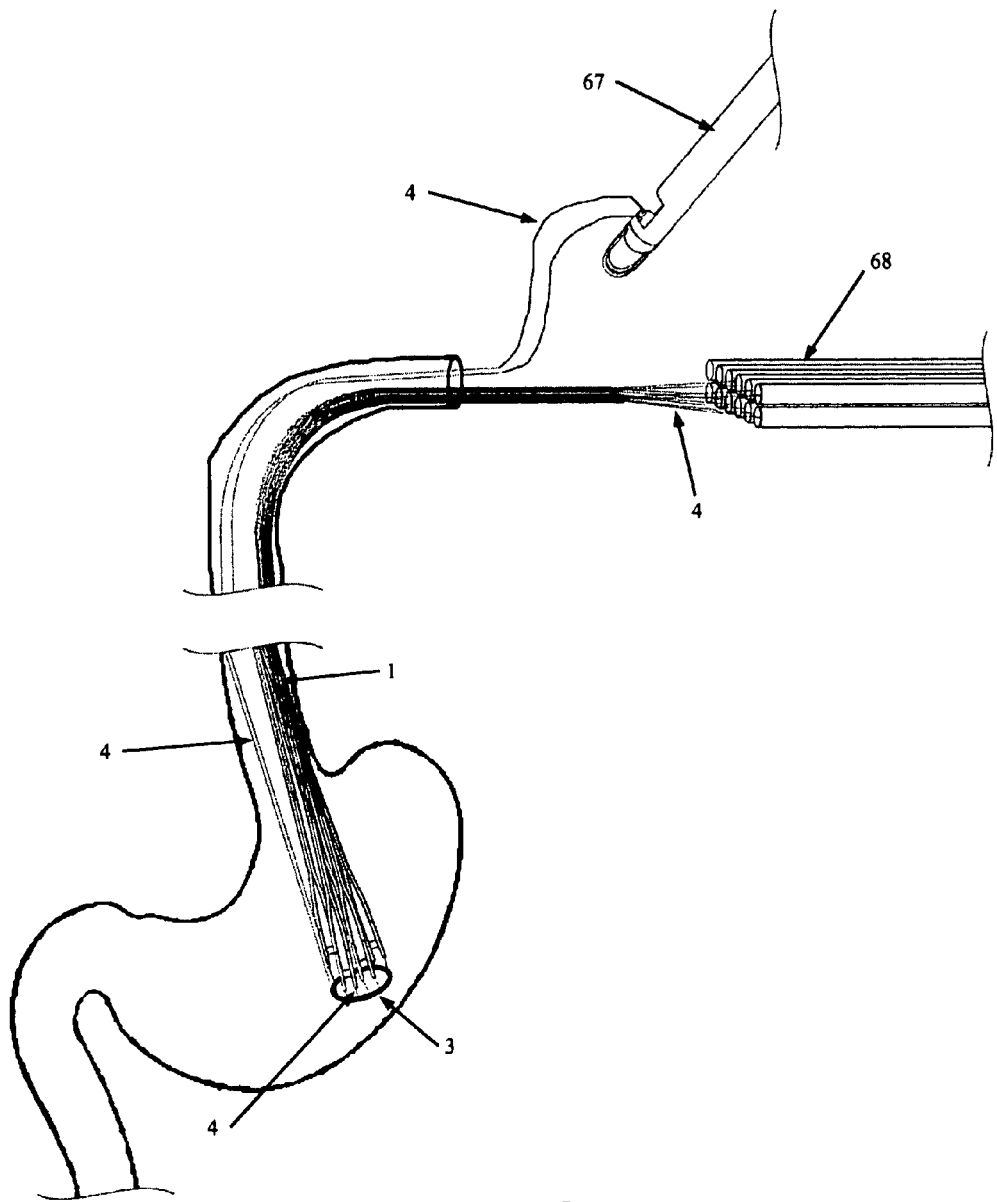
FIG. 36 illustrates a view of an alternative means of suturing a graft within a hollow organ using suture maintaining cannula sets without cannula warping function.

FIG. 36 illustrates a view of a system that may be employed for suturing a graft 3, 35 within a hollow organ or body cavity using a suturing device 67 that does not function using individual cannula unit and suction capsule components, but is constructed as one unit. The suturing device 67 is simply reloaded outside of the patient after each successive suture bite, then reinserted into the suturing site. A series of tubes 68 may be incorporated outside of the patient to organize and maintain the suture needles.

The series of tubes 68 may be utilized in all the embodiments of the device described. The tube or series of tubes 68 may facilitate organization of needles and sutures and also may help maintain sterility of the needles and sutures outside of the patient's body. The tube or series of tubes 68 may be able to be supplied to the field such that the interior lumens of the tube or tubes 68 are sterile. The tubes 68 may be configured in a linear fashion of configured so that they are spread out radially from one another.

What is claimed is:

1. A device for suturing within a hollow organ, comprising:
   a delivery cannula;
   a receiving cannula; and
   an elongated tube coupled to a linear suction capsule component, comprising a distal end, a proximal end, and a suction port,
   wherein the delivery cannula has a delivery cannula distal end comprised of a looping section, and the delivery cannula is attached to a warping cable, wherein by pulling the warping cable, the delivery cannula distal end bends and creates a loop around the distal end of the elongated tube, and, the delivery cannula distal end is disposed on one side of the suction port, and wherein the receiving cannula has a receiving cannula distal end that is configured to be disposed on a second side of the suction port, and wherein the linear suction capsule component is releasably held to the delivery cannula component and the receiving cannula component.

2. The device of claim 1, further comprising a graft disposed at the delivery cannula distal end.

3. The device of claim 2, further comprising a suture configured to pass through the delivery cannula, the graft, and the receiving cannula.

4. The device of claim 3, wherein the suture comprises a first needle coupled to a first end of the suture and a second needle coupled to a second end of the suture.

5. The device of claim 1, further comprising:
   a needle; and
   a suture coupled to one end of the needle,
   wherein the needle is configured to be inserted into the delivery cannula by backing the needle into the delivery cannula distal end, wherein the needle may be subsequently advanced across the suction port, and into the receiving cannula distal end.

6. The device of claim 1, further comprising a tubular structure coupled to a proximal end of the suction component.

7. The device of claim 6, further comprising an endoscope coupled to the tubular structure.

8. The device of claim 6, wherein the tubular structure comprises a flexible plastic.

9. The device of claim 1, wherein the warping cable is coupled to the delivery cannula substantially at the delivery cannula distal end.

10. The device of claim 9, further comprising a warping cable control lever coupled a proximal end of the warping cable.

11. The device of claim 1, wherein suction component comprises a groove that receives the delivery cannula distal end and the receiving cannula distal end.

* * * * *